United States Patent [19]
Dean et al.

[11] Patent Number: 6,083,480
[45] Date of Patent: *Jul. 4, 2000

[54] CALCITONIN RECEPTOR BINDING REAGENTS

[75] Inventors: Richard T. Dean, Bedford; Larry R. Bush, Exeter; Daniel A. Pearson; John Lister-James, both of Bedford, all of N.H.

[73] Assignee: Diatide, Inc., Londonderry, N.H.

[*] Notice: This patent is subject to a terminal disclaimer.

[21] Appl. No.: 08/847,007

[22] Filed: May 1, 1997

[51] Int. Cl.[7] .......................... A61K 51/00; A61M 36/14
[52] U.S. Cl. .......................... 424/1.69; 534/10; 534/14; 530/300; 530/307; 530/317; 424/1.65; 424/1.11
[58] Field of Search .................. 424/1.11, 1.65, 424/1.69, 9.1, 9.3, 9.4, 9.5, 1.49; 534/1.53, 7, 10–16; 530/300, 311, 317, 307, 324–330, 333–334, 338; 206/223, 569, 570; 514/13

[56] References Cited

U.S. PATENT DOCUMENTS

| | | | |
|---|---|---|---|
| 4,086,221 | 4/1978 | Sakakibara et al. | |
| 4,277,393 | 7/1981 | Sakakibara et al. | |
| 4,663,309 | 5/1987 | Kaiser et al. | 514/11 |
| 4,988,496 | 1/1991 | Srinivasan et al. | 424/1.11 |
| 5,443,815 | 8/1995 | Dean et al. | 424/1.41 |
| 5,443,816 | 8/1995 | Zamora et al. | 424/1.69 |
| 5,541,159 | 7/1996 | Albert et al. | |
| 5,698,521 | 12/1997 | McKernan et al. | 514/13 |
| 5,759,516 | 6/1998 | Zamora et al. | 424/1.69 |
| 5,807,537 | 9/1998 | Dean et al. | 424/1.69 |

FOREIGN PATENT DOCUMENTS

| | | |
|---|---|---|
| 0 181 121 A3 | 5/1986 | European Pat. Off. |
| 0 347 105 A2 | 12/1989 | European Pat. Off. |
| 0 315 687 B1 | 1/1994 | European Pat. Off. |
| 0 370 165 B1 | 1/1994 | European Pat. Off. |
| WO 94/18959 | 9/1994 | WIPO |
| WO 95/33497 | 12/1995 | WIPO |
| WO 96/04308 | 2/1996 | WIPO |

OTHER PUBLICATIONS

Cohen, et al. (1996) "Iodocalcitonin Binds to Human Calcitonin Receptors with Higher Affinity than Calcitonin" Endocrinology, 137, 4507–4510.

Findlay, et al. (1981) "Calcitonin Binding and Degradation by Two Cultured Human Breast Cancer Cell Lines (MCF 7 and T 47D)" Biochem. Jnl., 196, 513–520.

Paulin, et al., (1978) "Preliminary Study on Synthetic Calcitonin in the Rabbit and in Man" Bull. Soc. Med. Afr. Noire Lgue Frxe, 23, 246–251, translation enclosed.

Potts, John T. Jr., (1992) "Chemistry of the Calcitonins" Bone and Mineral, 16 169–173.

Zaidi, et al., (1987) "Biology of Peptides from the Calcitonin Genes" Quarterly Jnl. of Experimental Physiology, 72, 371–408.

Yates, et al. (1990) A Noncyclical Analog of Salmon Calcitonin ($N^{\alpha 1}$–Propionyl Di–Ala$^{1,7}$, des–Leu$^{19}$sCT) Retains Full Potency without Inducing Anorexia in Rats.

Dox et al., The Harper Collins Illustrated Medical Dictionary, p. 80, 1993.

*Primary Examiner*—Jose 'G. Dees
*Assistant Examiner*—Dameron Jones
*Attorney, Agent, or Firm*—Patricia A. McDaniels; Kevin E. Noonan

[57] ABSTRACT

This invention relates to radiotherapeutic reagents and peptides, radiodiagnostic reagents and peptides, and methods for producing labeled radiodiagnostic and radiotherapeutic agents. Specifically, the invention relates to calcitonin receptor binding compounds, preferably peptides, derivatives and analogues of calcitonin, and embodiments of such compounds radiolabeled with a radioisotope, as well as methods and kits for making, radiolabeling and using such compounds, particularly peptides for radiodiagnostic and radiotherapeutic purposes. The invention specifically relates to calcitonin receptor binding peptide derivatives and analogues of calcitonin radiolabeled with technetium-99m and uses thereof as scintigraphic imaging agents. The invention also specifically relates to calcitonin receptor binding peptide derivatives and analogues of calcitonin radiolabeled with cytotoxic radioisotopes such as rhenium-186 ($^{186}$Re) and rhenium-188 ($^{188}$Re) for use as radiotherapeutic agents. Methods and kits for making, radiolabeling and using such peptides diagnostically and therapeutically in a mammalian body are also provided.

38 Claims, 1 Drawing Sheet

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 32 amino acids
      (B) TYPE: amino acid
      (D) TOPOLOGY: circular (ii) MOLECULE TYPE: peptide (ix) FEATURE:
      (A) NAME/KEY: Modified-site
      (B) LOCATION: 1..7
      (D) OTHER INFORMATION: /label= Disulfide bond
          /note= "A disulfide bond exists between the
          two sulfur atoms of the cysteine residues;

(ix) FEATURE:
      (A) NAME/KEY: Modified-site
      (B) LOCATION: 32
      (D) OTHER INFORMATION: /label= Amide
          /note= "The carboxyl terminus is modified to an
          amide"

(xi) SEQUENCE DESCRIPTION: SEQ ID NO:1:

Cys Gly Asn Leu Ser Thr Cys Met Leu Gly Thr Tyr Thr Gln Asp Phe Asn
1               5                   10                  15

Lys Phe His Thr Phe Pro Gln Thr Ala Ile Gly Val Gly Ala Pro
            20                  25                  30

(2) INFORMATION FOR SEQ ID NO:2:

(i) SEQUENCE CHARACTERISTICS:
      (A) LENGTH: 32 amino acids
      (B) TYPE: amino acid
      (D) TOPOLOGY: circular (ii) MOLECULE TYPE: peptide (ix) FEATURE:
      (A) NAME/KEY: Modified-site
      (B) LOCATION: 1..7
      (D) OTHER INFORMATION: /label= Disulfide bond
          /note= "A disulfide bond exists between the
          two sulfur atoms of the cysteine residues;

(ix) FEATURE:
      (A) NAME/KEY: Modified-site
      (B) LOCATION: 32
      (D) OTHER INFORMATION: /label= Amide
          /note= "The carboxyl terminus is modified to an
          amide"

(xi) SEQUENCE DESCRIPTION: SEQ ID NO:2:

Cys Ser Asn Leu Ser Thr Cys Val Leu Gly Lys Leu Ser Gln Glu Leu His
1               5                   10                  15

Lys Leu Gln Thr Tyr Pro Arg Thr Asn Thr Gly Ser Gly Thr Pro
            20                  25                  30

(2) INFORMATION FOR SEQ ID NO:3:

(i) SEQUENCE CHARACTERISTICS:
      (A) LENGTH: 32 amino acids
      (B) TYPE: amino acid
      (D) TOPOLOGY: circular

```
            (ii) MOLECULE TYPE: peptide (ix) FEATURE:
                 (A) NAME/KEY: Modified-site
                 (B) LOCATION: 1..7
                 (D) OTHER INFORMATION: /label= Disulfide bond
                     /note= "A disulfide bond exists between the
                     two sulfur atoms of the cysteine residues;

(ix) FEATURE:
                 (A) NAME/KEY: Modified-site
                 (B) LOCATION: 32
                 (D) OTHER INFORMATION: /label= Amide
                     /note= "The carboxyl terminus is modified to an
                     amide"

(xi) SEQUENCE DESCRIPTION: SEQ ID NO:3:

Cys Ser Asn Leu Ser Thr Cys Val Leu Gly Lys Leu Ser Gln Glu Leu His
1               5                   10                  15

Lys Leu Gln Thr Tyr Pro Arg Thr Asp Val Gly Ala Gly Thr Pro
            20                  25                  30

(2) INFORMATION FOR SEQ ID NO:4:

(i) SEQUENCE CHARACTERISTICS:
                (A) LENGTH: 31 amino acids
                (B) TYPE: amino acid
                (D) TOPOLOGY:circular (ii) MOLECULE TYPE: peptide (ix) FEATURE:
                 (A) NAME/KEY: Modified-site
                 (B) LOCATION: 1..6
                 (D) OTHER INFORMATION: /label= Cyclic
                     /note= "The amino terminus and the side chain sulfur
                     atom of homohomocysteine are covalently linked via
                     a acetyl group."

(ix) FEATURE:
                 (A) NAME/KEY: Modified-site
                 (B) LOCATION: 6
                 (D) OTHER INFORMATION: /label= Variant residues
                     /note= "The residue is homohomocysteine."

(ix) FEATURE:
                 (A) NAME/KEY: Modified-site
                 (B) LOCATION: 13
                 (D) OTHER INFORMATION: /label= BAT
                     /note= "The side chain sulfur atom of the cysteine is
                     covalently linked to a BAT chelating moiety."

(ix) FEATURE:
                 (A) NAME/KEY: Modified-site
                 (B) LOCATION: 31
                 (D) OTHER INFORMATION: /label= Amide
                     /note= "The carboxyl terminus is modified to an
                     amide"

(xi) SEQUENCE DESCRIPTION: SEQ ID NO:4:

Ser Asn Leu Ser Thr Xaa Val Leu Gly Lys Leu Ser Cys Glu Leu His Lys
1               5                   10                  15

Leu Gln Thr Tyr Pro Arg Thr Asn Thr Gly Ser Gly Thr Pro
            20                  25                  30

(2) INFORMATION FOR SEQ ID NO:5:

(i) SEQUENCE CHARACTERISTICS:
                (A) LENGTH: 31 amino acids
                (B) TYPE: amino acid
                (D) TOPOLOGY:circular (ii) MOLECULE TYPE: peptide
```

```
    (ix) FEATURE:
         (A) NAME/KEY: Modified-site
         (B) LOCATION: 1..6
         (D) OTHER INFORMATION: /label= Cyclic
                /note= "The amino terminus and the side chain sulfur
                atom of homohomocysteine are covalently linked via
                a acetyl group."

(ix) FEATURE:
         (A) NAME/KEY: Modified-site
         (B) LOCATION: 6
         (D) OTHER INFORMATION: /label= Variant residues
                /note= "The residue is homohomocysteine."

(ix) FEATURE:
         (A) NAME/KEY: Modified-site
         (B) LOCATION: 31
         (D) OTHER INFORMATION: /label= Amide
                /note= "The carboxyl terminus is modified to an
                amide"

(xi) SEQUENCE DESCRIPTION: SEQ ID NO:5:

Ser Asn Leu Ser Thr Xaa Val Leu Gly Lys Leu Ser Cys Glu Leu His Lys
1               5                   10                  15

Leu Gln Thr Tyr Pro Arg Thr Asn Thr Gly Ser Gly Thr Pro
        20                  25                  30

(2) INFORMATION FOR SEQ ID NO:6:

(i) SEQUENCE CHARACTERISTICS:
         (A) LENGTH: 31 amino acids
         (B) TYPE: amino acid
         (D) TOPOLOGY:circular (ii) MOLECULE TYPE: peptide (ix) FEATURE:
         (A) NAME/KEY: Modified-site
         (B) LOCATION: 1..6
         (D) OTHER INFORMATION: /label= Cyclic
                /note= "The amino terminus and the side chain sulfur
                atom of homohomocysteine are covalently linked via
                a acetyl group."

(ix) FEATURE:
         (A) NAME/KEY: Modified-site
         (B) LOCATION: 6
         (D) OTHER INFORMATION: /label= Variant residues
                /note= "The residue is homohomocysteine."

(ix) FEATURE:
         (A) NAME/KEY: Modified-site
         (B) LOCATION: 31
         (D) OTHER INFORMATION: /label= Amide
                /note= "The carboxyl terminus is modified to an
                amide"

(xi) SEQUENCE DESCRIPTION: SEQ ID NO:6:

Ser Asn Leu Ser Thr Xaa Val Leu Gly Lys Leu Ser Cys Glu Leu His Lys
1               5                   10                  15

Leu Gln Thr Tyr Pro Arg Thr Asn Thr Gly Ser Gly Thr Pro
        20                  25                  30

(2) INFORMATION FOR SEQ ID NO:7:

(i) SEQUENCE CHARACTERISTICS:
         (A) LENGTH: 31 amino acids
         (B) TYPE: amino acid
         (D) TOPOLOGY:circular (ii) MOLECULE TYPE: peptide
```

```
        (ix) FEATURE:
              (A) NAME/KEY: Modified-site
              (B) LOCATION: 1..6
              (D) OTHER INFORMATION: /label= Cyclic
                  /note= "The amino terminus and the side chain sulfur
                  atom of homohomocysteine are covalently linked via
                  a acetyl group."

(ix) FEATURE:
              (A) NAME/KEY: Modified-site
              (B) LOCATION: 31
              (D) OTHER INFORMATION: /label= Amide
                  /note= "The carboxyl terminus is modified to an
                  amide"

(xi) SEQUENCE DESCRIPTION: SEQ ID NO:7:

Ser Asn Leu Ser Thr Cys Val Leu Gly Lys Leu Ser Cys Glu Leu His Lys
1               5                   10                  15

Leu Gln Thr Tyr Pro Arg Thr Asn Thr Gly Ser Gly Thr Pro
            20                  25                  30

(2) INFORMATION FOR SEQ ID NO:8:

(i) SEQUENCE CHARACTERISTICS:
              (A) LENGTH: 31 amino acids
              (B) TYPE: amino acid
              (D) TOPOLOGY:circular (ii) MOLECULE TYPE: peptide (ix) FEATURE:
              (A) NAME/KEY: Modified-site
              (B) LOCATION: 1..6
              (D) OTHER INFORMATION: /label= Cyclic
                  /note= "The amino terminus and the side chain carboxyl
                  group of 2-aminosuberic acid are covalently linked via
                  a amide bond."

(ix) FEATURE:
              (A) NAME/KEY: Modified-site
              (B) LOCATION: 6
              (D) OTHER INFORMATION: /label= Variant residues
                  /note= "The residue is 2-aminosuberic acid"

(ix) FEATURE:
              (A) NAME/KEY: Modified-site
              (B) LOCATION: 31
              (D) OTHER INFORMATION: /label= Amide
                  /note= "The carboxyl terminus is modified to an
                  amide"

(xi) SEQUENCE DESCRIPTION: SEQ ID NO:8:

Ser Asn Leu Ser Thr Xaa Val Leu Gly Lys Leu Ser Cys Glu Leu His Lys
1               5                   10                  15

Leu Gln Thr Tyr Pro Arg Thr Asn Thr Gly Ser Gly Thr Pro
            20                  25                  30
```

CALCITONIN RECEPTOR BINDING REAGENTS

BACKGROUND OF THE INVENTION

1. Field of the Invention

This invention relates to radiotberapeutic agents and peptides, radiodiagnostic agents and peptides, and methods for producing such labeled radiodiagnostic and radiotherapeutic agents. Specifically, the invention relates to calcitonin receptor binding peptides and derivatives and analogues thereof, and embodiments of such peptides labeled with gamma-radiation emitting isotopes such as technetium-99m (Tc-99m), as well as methods and kits for making, radiolabeling and using such peptides to image sites in a mammalian body. The invention also relates to calcitonin receptor binding peptides and derivatives and analogues thereof, labeled with cytotoxic radioisotopes such as rhenium-186 ($^{186}$Re) and rhenium-188 ($^{188}$Re), and methods and kits for making, radiolabeling and using such peptides therapeutically in a mammalian body.

2. Description of the Prior Art

Calcitonin (CT) is a peptide produced in the thyroid, the secretion of which results in inhibition of bone resorption and lowering of plasma calcium concentration (see Mone Zaidi et al., in *Vitamins and Hormones* v.46, 1991, Academic Press: New York, pp. 87–164). These effects are brought about via specific receptor-mediated processes in two major target organs: bone (in osteoclasts) and kidney. In bone, CT inhibits resorption (removal) of calcium by osteoclasts from plasma; in kidney, CT inhibits resorption of filtered divalent calcium ions ($Ca^{2+}$) in the collecting ducts. Small amounts of CT have been administered to animals and humans without toxic effects. This result is due in part from the fact that the physiological effects of calcitonin are subtle even at maximum receptor occupancy and occur over a long time course. The major localization sites for administered CT are kidney, liver and the epiphyses of the long bones. Intravenously-administered calcitonin clears the blood rapidly and is excreted primarily in urine.

Human CT (hCT) is a 32 amino acid peptide containing a disulfide-cyclized heptapeptide amino terminus. CT from two other species (salmon and eel) are 50% homologous to the hCT amino acid sequence, but have a 10-fold higher affinity to CT receptor (CTR; $IC_{50}$=0.78 nM; Findlay et al., ibid.). These peptides have the following amino acid sequences:

hCT CGNLSTCMLG.TYTQD.FNKFH.TFPQT.AIGVG. AP.amide (SEQ ID NO. 1)

sCT CSNLSTCVLG.KLSQE.LHKLQ.TYPRT.NTGSG. TP.amide (SEQ ID NO. 2)

eCT CSNLSTCVLG.KLSQE.LHKLQ.TYPRT.DVGAG. TP.amide (SEQ ID NO. 3)

(where single-letter abbreviations for amino acids can be found in Zubay, *Biochemistry* 2d ed., 1988, MacMillan Publishing: New York, p. 33, and where the underlined amino acids between the two cysteine residues in the amino terminal portion of the peptide represent a disulfide bond).

It has been shown that $(ASu^{1,7})eCT$ (wherein the amino terminal cysteine residue is removed, the cysteine residue at position 7 has been substituted with 2-amino suberic acid and the cyclic disulfide has been replaced with a cyclic amide formed between the amino terminus and the side chain carboxylic acid moiety of the 2-amino suberic acid residue) binds to CT receptor with equal affinity as eCT itself and is much more resistant to proteolytic degradation at the receptor than the native peptide (Morikawa et al., 1976, *Experientia* 32: 1104–1106). There is also some evidence that truncated calcitonin peptide derivatives (such as Cbz-LHKLQY-OMe) retain substantial receptor binding activity (see Epand et al., 1988, *J. Med. Chem.* 31: 1595–1598).

CT peptides are readily synthesized using automated solid phase peptide synthesis, with the chemically-labile disulfide replaced with a stable congener. Position 14 of the peptide can be substituted without substantial loss of biological activity. (Moseley et al., 1982, *J. Biol. Chem.* 257: 5846–5851).

There is a need in the art for diagnostic agents that allow the detection and localization of tumors in a mammalian, particularly human, body. Current imaging modalities, such as computer-assisted tomography and magnetic resonance imaging can detect a lesion but cannot provide any information of whether a lesion is malignant, for example. Metastatic disease in particular is often difficult to detect using conventional imaging modalities. There is a need for diagnostic imaging agents that allow characterization of such lesions in vivo, preferably non-invasively, and particularly with regard to the detection of metastatic disease. Recently, it has been reported that cell surface receptors for CT are overexpressed in certain breast, lung, ovarian and lymphoma cancer cell lines (Findlay et al., 1981, *Biochem. J.* 196: 513–520). The present inventors have determined that the presence of calcitonin receptors on the cell surface of tumor cells (in lung and ovarian adenocarcinoma, breast cancers and lymphomas, for example) can be exploited as a marker to locate and identify such tumor cells in vivo, by providing detectably-labeled calcitonin receptor-binding peptides as described herein.

A variety of radionuclides are known to be useful for radioimaging, including $^{67}$Ga, $^{99m}$Tc (Tc-99m), $^{111}$In and $^{123}$I. A number of factors must be considered for optimal radioimaging in humans. To maximize the efficiency of detection, a radionuclide that emits gamma energy in the 200 to 200 keV range is preferred. To minimize the absorbed radiation dose to the patient, the physical half-life of the radionuclide must be as short as the imaging procedure will allow. To allow for examinations to be performed on any day and at any time of the day, it is advantageous to have a source of the radionuclide always available at the clinical site.

Radioiodination of calcitonin peptides has been shown in the prior art.

Hunt et al., 1977, *Br. J. Cancer* 35: 401–406 describe radioiodination of calcitonin.

Findlay et al., 1981, *Biochem. J.* 196: 513–520 described use of radioiodinated calcitonin to demonstrate calcitonin receptor binding in human breast cancer cell lines.

Tc-99m is a preferred radionuclide because it emits gamma radiation at 140 keV, it has a physical half-life of 6 hours, and it is readily available on-site using a molybdenum-99/technetium-99m generator. Other radionuclides used in the prior art for radioimaging are less advantageous than Tc-99m. This is because the physical half-life of some such radionuclides is longer, resulting in a greater amount of absorbed radiation dose to the patient (e.g., indium-111). Alternatively, the gamma radiation energies of such alternate radionuclides are significantly lower (e.g., iodine-125) or higher (e.g., iodine-131) than Tc-99m and are thereby inappropriate for quality scintigraphic imaging. Lastly, many disadvantageous radionuclides cannot be produced using an on-site generator.

Tc-99m is a transition metal that is advantageously chelated by a metal complexing moiety. Radiolabel complexing moieties capable of binding Tc-99m can be covalently linked to various specific binding compounds to provide a means for radiolabeling such specific binding compounds. This is because the most commonly available chemical species of Tc-99m, pertechnetate ($TcO_4^-$), cannot bind directly to most specific binding compounds strongly enough to be useful as a radiopharmaceutical. Complexing of Tc-99m with radiolabel complexing moieties typically entails chemical reduction of the pertechnetate using a reducing agent such as stannous chloride.

Although Tc-99m is the preferred radionuclide for scintigraphic imaging, it has not been widely used for labeling peptides (see Lamberts, 1991, J. Nucl. Med. 32: 1189–1191). This is because methods known in the prior art for labeling larger protein molecules (i.e., >10,000 daltons in size) with Tc-99m are not suitable for labeling peptides and other small molecules having a molecular size less than 10,000 daltons. Consequently, it is necessary to radiolabel most peptides by covalently attaching a radionuclide chelating moiety to the peptide, and so that the chelator is incorporated site-selectively at a position in the peptide that will not interfere with the specific binding properties of the peptide.

Methods for labeling peptides with Tc-99m are disclosed in co-owned U.S. Pat. Nos. 5,225,180, 5,405,597, 5,443,815, 5,508,020, 5,561,220, 5,620,675, and in co-pending U.S. patent applications Ser. Nos. 07/653,012, now abandoned, which issued as U.S. Pat. No. 5,811,394; 07/851,074, now abandoned, a divisional of which issued as U.S. Pat. No. 5,711,931; 07/871,282, a divisional of which issued as U.S. Pat. No. 5,780,007; 07/886,752, now abandoned which issued as U.S. Pat. No. 5,849,260; 07/902,935, which issued as U.S. Pat. No. 5,716,596; 07/955,466, now abandoned; 08/019,864, which issued as U.S. Pat. No. 5,552,525; 08/044,825 now abandoned, which issued as U.S. Pat. No. 5,645,815; 08/095,760, which issued as U.S. Pat. No. 5,620,675; 08/210,822, now abandoned; and PCT International Applications PCT/US92/00757, PCT/US92/10716, PCT/US93/02320, PCT/US93/03687, PCT/US93/04794, PCT/US93/05372, PCT/US93/06029, PCT/US93/09387, and PCT/US94/01894, which are hereby incorporated by reference.

Methods for preparing Tc-99m complexes are known in the art.

Byrne et al., U.S. Pat. Nos. 4,434,151, 4,575,556 and 4,571,430 describe homocysteine thiolactone-derived bifunctional chelating agents.

Fritzberg, U.S. Pat. No. 4,444,690 describes a series of technetium-chelating agents based on 2,3-bis(mercaptoacetamido) propanoate.

Nosco et al., U.S. Pat. No. 4,925,650 describe Tc-99m chelating complexes.

Kondo et al., European Patent Application, Publication No. 483704 A1 disclose a process for preparing a Tc-99m complex with a mercapto-Gly-Gly-Gly moiety.

European Patent Application No. 84109831.2 describes bisamido, bisthiol Tc-99m ligands and salts thereof as renal finction monitoring agents.

Davison et al., 1981, Inorg. Chem. 20: 1629–1632 disclose oxotechnetium chelate complexes.

Fritzberg et al., 1982, J. Nucl. Med. 23: 592–598 disclose a Tc-99m chelating agent based on N, N'-bis(mercaptoacetyl)-2,3-diaminopropanoate.

Byrne et al., 1983, J. Nucl. Med. 24: P126 describe homocysteine-containing Tc-99m chelating agents.

Bryson et al., 1988, Inorg. Chem. 27: 2154–2161 describe neutral complexes of technetium-99 which are unstable to excess ligand.

Misra et al., 1989, Tet. Lett. 30: 1885–1888 describe bisamine bisthiol compounds for radiolabeling purposes.

The use of chelating agents for radiolabeling protein and other specific-binding compounds is known in the art.

Gansow et al., U.S. Pat. No. 4,472,509 teach methods of manufacturing and purifying Tc-99m chelate-conjugated monoclonal antibodies.

Stavrianopoulos, U.S. Pat. No. 4,943,523 teach detectable molecules comprising metal chelating moieties.

Fritzberg et al., European Patent Application No. 86100360.6 describe dithiol, diamino, or diamidocarboxylic acid or amine complexes useful for making technetiumlabeled imaging agents.

Albert et al., UK Patent Application 8927255.3 disclose radioimaging using somatostatin derivatives such as octreotide labeled with $^{111}$In via a chelating group bound to the amino-terminus.

Albert et al., European Patent Application No. WO 91/01144 disclose radioimaging using radiolabeled peptides related to growth factors, hormones, interferons and cytokines and comprised of a specific recognition peptide covalently linked to a radionuclide chelating group.

Fischman et al., International Patent Application, Publication No. W093/13317 disclose chemotactic peptides attached to chelating moieties.

Kwekkeboom et al., 1991, J. Nucl. Med. 32: 981 Abstract #305 relates to radiolabeling somatostatin analogues with [111]In.

Albert et al., 1991, Abstract LM10, 12th American Peptide Symposium: 1991 describe uses for $^{111}$In-labeled diethylene-triaminopentaacetic acid-derivatized somatostatin analogues.

Cox et al., 1991, Abstract, 7th International Symposium on Radiopharmacology, p. 16, disclose the use of, Tc-99m-, [131]I- and $^{111}$In-labeled somatostatin analogues in radiolocalization of endocrine tumors in vivo by scintigraphy.

Methods for labeling certain specific-binding compounds such as antibodies with Tc-99m are known in the prior art.

Hnatowich, U.S. Pat. No. 4,668,503 describe Tc-99m protein radiolabeling.

Tolman, U.S. Pat. No. 4,732,684 describe conjugation of targeting molecules and fragments of metallothionein.

Nicolotti et al., U.S. Pat. No. 4,861,869 describe bifunctional coupling agents useful in forming conjugates with biological molecules such as antibodies.

Fritzberg et al., U.S. Pat. No. 4,965,392 describe various S-protected mercaptoacetylglycylglycine-based chelators for labeling proteins.

Schochat et al., U.S. Pat. No. 5,061,641 disclose direct radiolabeling of proteins comprised of at least one "pendent" sulfhydryl group.

Fritzberg et al., U.S. Pat. No. 5,091,514 describe various S-protected mercaptoacetylglycylglycine-based chelators for labeling proteins.

Gustavson et al., U.S. Pat. No. 5,112,953 disclose Tc-99m chelating agents for radiolabeling proteins.

Kasina et al., U.S. Pat. No. 5,175,257 describe various combinations of targeting molecules and Tc-99m chelating groups.

Dean et al., U.S. Pat. No. 5,180,816 disclose methods for radiolabeling a protein with Tc-99m via a bifunctional chelating agent.

Sundrehagen, International Patent Application, Publication No. WO85/03231 disclose Tc-99m labeling of proteins.

Reno and Bottino, European Patent Application 87300426.1 disclose radiolabeling antibodies with Tc-99m.

Bremer et al., European Patent Application No. 87118142.6 disclose Tc-99m radiolabeling of antibody molecules.

Pak et al., European Patent Application No. WO 88/07382 disclose a method for labeling antibodies with Tc-99m.

Goedemans et al., PCT Application No. WO 89/07456 describe radiolabeling proteins using cyclic thiol compounds, particularly 2-iminothiolane and derivatives.

Dean et al., International Patent Application, Publication No. WO89/12625 teach bifunctional coupling agents for Tc-99m labeling of proteins.

Schoemaker et al., International Patent Application, Publication No. WO90/06323 disclose chimeric proteins comprising a metal-binding region.

Thornback et al., EPC Application No. 90402206.8 describe preparation and use of radiolabeled proteins using thiol-containing compounds, particularly 2-iminothiolane.

Gustavson et al., International Patent Application, Publication No. WO91/09876 disclose Tc-99m chelating agents for radiolabeling proteins.

Rhodes, 1974, Sem. Nucl. Med. 4: 281–293 teach the labeling of human serum albumin with technetium-99m.

Khaw et al., 1982, J. Nucl. Med. 23: 1011–1019 disclose methods for labeling biologically active macromolecules with Tc-99m.

Schwartz et al., 1991, Bioconjugate Chem. 2: 333 describe a method for labeling proteins with Tc-99m using a hydrazinonicotinamide group.

Attempts at labeling peptides have been reported in the prior art.

Ege et al., U.S. Pat. No. 4,832,940 teach radiolabeled peptides for imaging localized T-lymphocytes.

Morgan et al., U.S. Pat. No. 4,986,979 disclose methods for imaging sites of inflammation.

Flanagan et al., U.S. Pat. No. 5,248,764 describe conjugates between a radiolabel chelating moiety and atrial natiuretic factor-derived peptides.

Ranby et al., 1988, PCT/US88/02276 disclose a method for detecting fibrin deposits in an animal comprising covalently binding a radiolabeled compound to fibrin.

Lees et al., 1989, PCT/US89/01854 teach radiolabeled peptides for arterial imaging.

Morgan et al., International Patent Application, Publication No. WO90/10463 disclose methods for imaging sites of inflammation.

Flanagan et al., European Patent Application No. 90306428.5 disclose Tc-99m labeling of synthetic peptide fragments via a set of organic chelating molecules.

Stuttle, PCT Application, Publication No. WO 90/15818 suggests Tc-99m labeling of RGD-containing oligopeptides.

Rodwell et al., 1991, PCT/US91/03116 disclose conjugates of "molecular recognition units" with "effector domains".

Cox, International Patent Application No. PCT/US92/04559 discloses radiolabeled somatostatin derivatives containing two cysteine residues.

Rhodes et al., International Patent Application, Publication No. WO93/12819 teach peptides comprising metal ion-binding domains.

Lyle et al, International Patent Application, Publication No. WO93/15770 disclose Tc-99m chelators and peptides labeled with Tc-99m.

Coughlin et al, International Patent Application, Publication No. WO93/21151 disclose bifunctional chelating agents comprising thiourea groups for radiolabeling targeting molecules.

Knight et al., 1990, 37th Annual Meeting of the Society of Nuclear Medicine, Abstract #209, claim thrombus imaging using Tc-99m labeled peptides.

Babich et al., 1993, J. Nucl. Med. 34: 1964–1974 describe Tc-99m labeled peptides comprising hydrazinonicotinamide derivatives.

The present inventors have developed Tc-99m labeled, small, synthetic, calcitonin-derived peptides possessing both the capacity for high-affinity binding to calcitonin receptors and favorable pharmacokinetics to permit efficient in vivo localization at tumor sites in this art to provide more specific imaging of important tumor cell types. Such labeled peptides provide rapid, cost-effective, non-invasive diagnostic imaging procedures useful for initial disease staging and evaluation of metastatic spread of the disease. Such peptides also provide ways to assess the therapeutic effectiveness by non-invasive localization of CTR-expressing tumor cells following surgery, radiation therapy or chemotherapy.

Calcitonin receptor binding peptides and radiolabeled derivatives and analogues thereof can also be used therapeutically. For these applications, cytotoxic radioisotopes are advantageous, such as rhenium-186 and rhenium-188.

There remains a need for synthetic (to make routine manufacture practicable and to ease regulatory acceptance) calcitonin receptor binding compounds, including peptides, derivatives and analogues thereof to be used as scintigraphic agents particularly when radiolabeled with Tc-99m for use in imaging tumors in vivo, and as radiotherapeutic agents when radiolabeled with a cytotoxic radioisotope such as rhenium-186 and rhenium-188. Small synthetic calcitonin receptor binding peptides and derivatives and analogues of such calcitonin receptor binding peptides that specifically fulfill this need are provided by this invention.

SUMMARY OF THE INVENTION

The present invention provides radiopharmaceuticals that are radiometal-labeled calcitonin receptor binding compounds, preferably peptides, for radiotherapeutic and radiodiagnostic applications, in particular scintigraphic imaging applications. The invention also provides calcitonin receptor binding reagents comprised of the calcitonin receptor binding compounds, preferably calcitonin peptides, derivatives and analogues thereof, wherein such compounds are covalently linked to a chelating moiety. The invention provides such calcitonin receptor binding compounds, calcitonin receptor binding reagents and radiolabeled embodiments thereof that are scintigraphic imaging agents, radiodiagnostic agents and radiotherapeutic agents. In preferred embodiments, the calcitonin receptor binding compounds have a molecular weight of less than about 10,000 daltons.

Scintigraphic imaging agents of the invention comprise calcitonin receptor binding compounds, preferably peptides, radiolabeled with radionuclides such as technetium-99m. Radiotherapeutic agents of the invention comprise calcitonin receptor binding reagents radiolabeled with, for example, rhenium-186 or rhenium-188. Methods for making and using such calcitonin receptor binding compounds, calcitonin receptor binding reagents and radiolabeled embodiments thereof are also provided.

The invention provides a reagent for preparing a radiopharmaceutical, wherein the reagent is a synthetic, calcitonin receptor-binding compound, preferably a peptide, that is covalently linked to a chelating moiety capable of chelating a radiometal, preferably a technetium or rhenium radioisotope. The chelating moiety is incorporated into the reagent during synthesis of the reagent. In addition, the technetium- or rhenium-labeled radiopharmaceuticals of the invention have a calcitonin receptor binding affinity that is not less than about one-tenth the affinity of radioiodinated native calcitonin. Preferred embodiments of the radiolabeled embodiments of the reagents of the invention have a calcitonin receptor (CTR) binding affinity equal to or greater than native calcitonin or radioiodinated species thereof.

In preferred embodiments, the invention provides scintigraphic imaging agents comprising a reagent of the invention radiolabeled with Tc-99m. In other preferred embodiments, the invention provides radiotherapeutic agents comprising a reagent of the invention radiolabeled with a cytotoxic radioisotope selected from the group consisting of rhenium-186 and rhenium-188. Complexes of the reagent and radiolabels that are Tc-99m, Re-186 or Re-188 are provided, formed by reacting a reagent of the invention with the radiolabel in the presence of a reducing agent, for example, a stannous ion. Complexes of Tc-99m, Re-186 or Re-188 with the reagents of the invention are also provided as produced by ligand exchange of a prereduced radiolabel complex.

Thus, the invention also provides scintigraphic imaging agents comprising the calcitonin receptor binding compounds of the invention wherein the chelating moiety is stably complexed with Tc-99m.

The invention also provides radiotherapeutic agents that are the calcitonin receptor binding compounds of the invention radiolabeled with rhenium-186 or rhenium-188.

The invention also provides pharmaceutical compositions comprising the radiolabeled calcitonin receptor-binding compounds of the invention in a pharmaceutically acceptable carrier.

Another aspect of the present invention provides reagents for preparing radiotherapeutic and radiodiagnostic radiopharmaceuticals, including preferably scintigraphic imaging agents. Each such reagent is comprised of a compounds that specifically binds to a calcitonin receptor, preferably a peptide that is calcitonin, a calcitonin derivative or analog covalently linked to a chelating moiety.

A first aspect of the reagents provided by the invention for preparing radiolabeled agents are reagents that are each comprised of a calcitonin receptor-binding compound, preferably a peptide, as described above that is covalently linked to a chelating moiety having the formula:

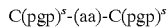

where $(pgp)^s$ is hydrogen or a thiol protecting group and (aa) is an α- or β-amino acid not comprising a thiol group. In a preferred embodiment, the amino acid is glycine. In another preferred embodiment, the agent is a scintigraphic imaging agent. In yet another preferred embodiment, the agent is a radiotherapeutic agent.

In a second embodiment, the invention provides calcitonin receptor binding reagents capable of being radiolabeled to form radiodiagnostic and radiotherapeutic agents, each comprising a calcitonin receptor binding compound, preferably a calcitonin peptide, derivative or analog thereof that is covalently linked to a chelating moiety containing a single thiol-containing group of formula:

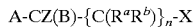

wherein A is H, HOOC, $H_2NOC$, (peptide)-NHOC, (peptide)-OOC, $R^e{}_2NCO$, or $R^d$; B is H, SH or —$NHR^c$, —$N(R^c)$-(peptide) or $R^d$; Z is H or $R^d$; X is SH or —$NHR^c$, —$N(R^c)$-(peptide) or $R^d$; $R^a$, $R^b$, $R^c$ and $R^d$ are independently H or straight or branched chain or cyclic lower alkyl; n is 0, 1 or 2; $R^e$ is $C_1$–$C_4$ alkyl, an amino acid or a peptide comprising 2 to about 10 amino acids; and: (1) where B is —$NHR^c$ or —$N(R^c)$-(peptide), X is SH and n is 1 or 2; (2) where X is —$NHR^c$ or —$N(R^c)$-(peptide), B is SH and n is 1 or 2; (3) where B is H or $R^d$, A is HOOC, $H_2NOC$, (peptide)-NHOC, or (peptide)-OOC, X is SH and n is 0 or 1; (4) where A is H or $R^d$, then where B is SH, X is —$NHR^c$ or —$N(R^c)$-(peptide) and where X is SH, B is —$NHR^c$ or —$N(R^c)$-(peptide) and n is 1 or 2; (5) where X is H or $R^d$, A is HOOC, $H_2NOC$, (peptide)-NHOC, or (peptide)-OOC and B is SH; (6) where Z is methyl, X is methyl, A is HOOC, $H_2NOC$, (peptide)-NHOC, or (peptide)-OOC and B is SH and n is 0; and (7) where B is SH, X is not SH and where X is SH, B is not SH. In a preferred embodiment, the agent is a scintigraphic imaging agent. In yet another preferred embodiment, the agent is a radiotherapeutic agent.

Preferred embodiments of this chelating moiety have a chemical formula that is:

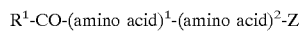

wherein (amino acid)$^1$ and (amino acid)$^2$ are each independently any primary α- or β-amino acid that does not comprise a thiol group, Z is a thiol-containing moiety that is cysteine, homocysteine, isocysteine, penicillamine, 2-mercaptoethylamine or 3-mercaptopropylamine, and $R^1$ is lower ($C^1$–$C^4$) alkyl, an amino acid or a peptide comprising 2 to 10 amino acids. When Z is cysteine, homocysteine, isocysteine or penicillamine, the carbonyl group of said moiety is covalently linked to a hydroxyl group, a $NR^3R^4$ group, wherein each of $R^3$ and $R^4$ are independently H or lower ($C^1$–$C^4$) alkyl, an amino acid or a peptide comprising 2 to 10 amino acids; or

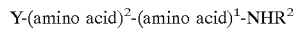

wherein Y is a thiol-containing moiety that is cysteine, homocysteine, isocysteine, penicillamine, 2-mercaptoacetate or 3-mercaptopropionate, (amino acid)$^1$ and (amino acid)$^2$ are each independently any primary α- or β-amino acid that does not comprise a thiol group, and $R^2$ is H or lower ($C^1$–$C^4$) alkyl, an amino acid or a peptide comprising 2 to 10 amino acids. When Y is cysteine, homocysteine, isocysteine or penicillamine, the amino group of said moiety is covalently linked to —H, an amino acid or a peptide comprising 2 to 10 amino acids.

In particular embodiments of this aspect of the invention, the chelating moiety has a formula that is:

IIa. -(amino acid)$^1$-(amino acid)$^2$-A-CZ(B)-{C($R^1R^2$)}$^n$-X},

IIb. -A-CZ(B)-{C($R^1R^2$)}$^n$-X}-(amino acid)$^1$-(amino acid)$^2$,

IIc. -(a primary α,ω- or β,ω-diamino acid)-(amino acid)$^1$-A-CZ(B)-{C($R^1R^2$)}$^n$-X}, or IId. -A-CZ(B)-{C($R^1R^2$)}$^n$-X}(amino acid)$^1$-(a primary α,β- or β,γ-diamino acid)

wherein (amino acid)$^1$ and (amino acid)$^2$ are each independently any naturally-occurring, modified, substituted or altered α- or β-amino acid not containing a thiol group; A is H, HOOC, $H_2NOC$, (amino acid or peptide)-NHOC, (amino acid or peptide)-OOC or $R^4$; B is H, SH or —$NHR^3$, —$N(R^3)$-(amino acid or peptide) or $R^4$; Z is H or $R^4$; X is SH or —$NHR^3$, —$N(R^3)$-(amino acid or peptide) or $R^4$; $R^1$, $R^2$, $R^3$ and $R^4$ are independently H or straight or branched chain or cyclic lower alkyl; n is an integer that is either 0, 1 or 2; (peptide) is a peptide of 2 to about 10 amino acids; and: (1) where B is —$NHR^3$ or —$N(R^3)$-(amino acid or peptide), X is SH and n is 1 or 2; (2) where X is —$NHR^3$ or —$N(R^3)$-(amino acid or peptide), B is SH and n is 1 or 2; (3) where B is H or $R^4$, A is HOOC, $H_2NOC$, (amino acid or peptide)-NHOC, (amino acid or peptide)-OOC, X is SH and n is 0 or 1; (4) where A is H or $R^4$, then where B is SH, X is —$NHR^3$ or —$N(R^3)$-(amino acid or peptide) and where X is SH, B is —$NHR^3$ or —$N(R^3)$-(amino acid or peptide) and n is 1 or 2; (5) where X is H or $R^4$, A is HOOC, $H_2NOC$, (amino acid or peptide)-NHOC, (amino acid or peptide)-OOC and B is SH; (6) where Z is methyl, X is methyl, A is HOOC, $H_2NOC$, (amino acid or peptide)-NHOC, (amino acid or peptide)-OOC and B is SH and n is 0; and (7) where B is SH, X is not SH and where X is SH, B is not SH.

Additional preferred embodiments include chelating moieties having the formula: -Gly-Gly-Cys-, Cys-Gly-Gly-, Gly-Gly-Cys-, -(ε-Lys)-Gly-Cys-, (δ-Orn)-Gly-Cys-, -(γ-Dab)-Gly-Cys-, and -(β-Dap)-Gly-Cys-. (In these formulae, it will be understood that ε-Lys represents a lysine residue in which the ε-amino group, rather than the typical α-amino group, is covalently linked to the carboxyl group of the adjacent amino acid to form a peptide bond; δ-Orn represents an ornithine residue in which the δ-amino group, rather than the typical α-amino group, is covalently linked to the carboxyl group of the adjacent amino acid to form a peptide bond; γ-Dab represents a 2,4-diaminobutyric acid residue in which the γ-amino group is covalently linked to the carboxyl group of the adjacent amino acid to form a peptide bond; and β-Dap represents a 1,3-diaminopropionic acid residue in which the β-amino group is covalently linked to the carboxyl group of the adjacent amino acid to form a peptide bond.)

Yet another embodiment of the invention provides calcitonin receptor binding reagents capable of being radiolabeled with a radioisotope for imaging sites within a mammalian body or for radiotherapeutic purposes, each comprising a calcitonin receptor binding compound having a molecular weight less than about 10,000 daltons and preferably calcitonin, a calcitonin derivative or a calcitonin analogue that is covalently linked to a chelating moiety that is a bisamino-bisthiol chelating moiety. The bisamino bisthiol chelating moiety in this embodiment of the invention has the formula:

$$\begin{array}{c} (CR_2)_n \\ NH \quad N—A—CO—X \\ (CR_2)_m \quad (CR_2)_p \\ S\text{-}(pgp)^s \quad S\text{-}(pgp)^s \end{array}$$

wherein each R can be independently H, $CH_3$ or $C_2H_5$; each $(pgp)^s$ can be independently a thiol protecting group or H; m, n and p are independently 2 or 3; A is linear or cyclic lower alkyl, aryl, heterocyclyl, combinations or substituted derivatives thereof; and X is peptide; or $$\begin{array}{c} (CR_2)_n \\ NH \quad N—A—CH(V)NHR' \\ (CR_2)_m \quad (CR_2)_p \\ SH \quad SH \end{array}$$

wherein each R is independently H, $CH_3$ or $C_2H_5$; m, n and p are independently 2 or 3; A is linear or cyclic lower alkyl, aryl, heterocyclyl, combinations or substituted derivatives thereof; V is H or CO-peptide; R' is H or peptide; provided that when V is H, R' is peptide and when R' is H, V is CO-peptide. For purposes of this invention, chelating moieties having these structures will be referred to as "BAT" moieties. In a preferred embodiment, the agent is a scintigraphic imaging agent. In yet another preferred embodiment, the agent is a radiotherapeutic agent.

The invention also provides calcitonin receptor binding reagents comprising radiometal chelating moieties including diethylenetriaminepentaacetic acid (DTPA)

$(HOOCCH_2)_2N(CR_2)(CR_2)N(CH_2COOH)(CR_2)(CR_2)N(CH_2COOH)_2$ ethylenediaminetetraacetic acid (EDTA)

$(HOOCCH_2)_2N(CR_2)(CR_2)N(CH_2COOH)_2$ where each R is independently H, $C_1$ to $C_4$ alkyl, or aryl and one R is covalently linked to a calcitonin receptor binding compound;

1,4,7,10-tetraazadodecanetetraacetic acid

[structure]

R = H or lower alkyl and one R a link to a calcitonin receptor binding compound;

and

[structure]

where n is an integer that is 2 or 3 and where each R is independently H, $C_1$ to $C_4$ alkyl, or aryl and one R is covalently linked to calcitonin receptor binding compound, or desferrioxamine.

The invention also provides radiopharmaceutical agents and reagents for preparing such radiopharmaceuticals comprising a calcitonin receptor binding compound having a molecular weight less than about 10,000 daltons and preferably a calcitonin peptide, derivative or analog covalently linked to a chelating moiety selected from the group consisting of:

(i) a group having the formula:

[structure]

(ii) a group having the formula:

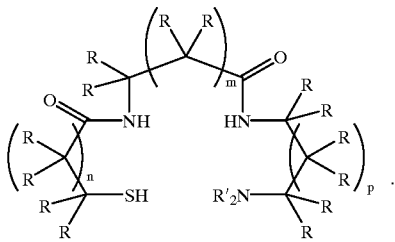

II wherein n, m and p are each integers that are independently 0 or 1; each R' is independently H, lower alkyl, $C_2$–$C_4$ hydroxyalkyl, or $C_2$–$C_4$ alkoxyalkyl, and each R is independently H or R", where R" is substituted or unsubstituted lower alkyl or phenyl not comprising a thiol group, and one R or R' is L, where L is a bivalent linker moiety linking the metal chelator to the targeting moiety and wherein when one R' is L, $NR'_2$ is an amine.

In preferred embodiments, L is a $C_1$–$C_6$ linear, branched chain or cyclic alkyl group, a carboxylic ester, a carboxamide, a sulfonamide, an ether, a thioether, an amine, an alkene, an alkyne, a 1,2-, 1,3- or 1,4-linked, optionally substituted, benzene ring, or an amino acid or peptide of 2 to about 10 amino acids, or combinations thereof.

In preferred embodiments, R" is a $C_1$–$C_6$ linear, branched or cyclic alkyl group; a —$C_qOC_r$—, —$C_qNHC_r$— or —$C_qSC_r$— group, where q and r are integers each independently 1 to 5 wherein the sum of q+r is not greater than 6; ($C_1$–$C_6$) alkyl-X, where X is a hydroxyl group, a substituted amine, a guanidine, an amidine, a substituted thiol group, or a carboxylic acid, ester, phosphate, or sulfate group; a phenyl group or a phenyl group substituted with a halogen, hydroxyl, substituted amine, guanidine, amidine, substituted thiol, ether, phosphate, or sulfate group; an indole group; a $C_1$–$C_6$ heterocyclic group containing 1 to 3 nitrogen, oxygen or sulfur atoms or combinations thereof.

Preferred chelating moieties of the invention include chelators having the formula:

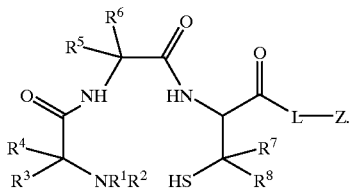

III wherein $R^1$ and $R^2$ are each independently H, lower alkyl, $C_2$–$C_4$ hydroxyalkyl, or $C_2$–$C_4$ alkoxyalkyl; $R^3$, $R^4$, $R^5$ and $R^6$ are independently H, substituted or unsubstituted lower alkyl or phenyl not comprising a thiol group; $R^7$ and $R^8$ are each independently H, lower alkyl, lower hydroxyalkyl or lower alkoxyalkyl; L is a bivalent linker group and Z is a calcitonin peptide.

Additional preferred metal chelators of the invention include chelators of formula:

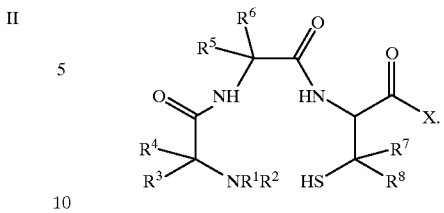

IV wherein $R^1$ and $R^2$ are each independently H, lower alkyl, $C_2$–$C_4$ hydroxyalkyl, or $C_2$–$C_4$ alkoxyalkyl; $R^3$, $R^4$, $R^5$ and $R^6$ are independently H, substituted or unsubstituted lower alkyl or phenyl not comprising a thiol group, and one of $R^3$, $R^4$, $R^5$ or $R^6$ is Z—L—HN(CH$_2$)$_n$—, where L is a bivalent linker group, Z is a calcitonin peptide, and n is an integer from 1 to 6; $R^7$ and $R^8$ are each independently H, lower alkyl, lower hydroxyalkyl or lower alkoxyalkyl; and X is an amino group, a substituted amino group or —$NR^1$—Y, where Y is an amino acid, an amino acid amide, or a peptide comprising from 2 to 10 amino acids.

More preferred metal chelators of the invention include chelators having the formula:

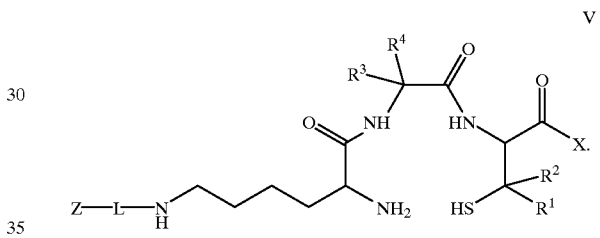

V wherein $R^1$ and $R^2$ are each independently H, lower alkyl, lower hydroxyalkyl, or lower alkenylalkyl; $R^3$ and $R^4$ are independently H, substituted or unsubstituted lower alkyl or phenyl not comprising a thiol group; n is an integer from 1 to 6; L is a bivalent linker group; and Z is a calcitonin peptide moiety.

Additional more preferred chelating moieties include chelators of formula:

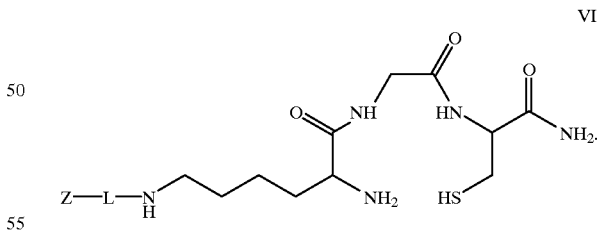

VI wherein L is a bivalent linker group and Z is a calcitonin peptide moiety.

Most preferred chelating moieties of the invention include chelators having the following formulae:

(amino acid)$^1$-(amino acid)$^2$-cysteine-,
(amino acid)$^1$-(amino acid)$^2$-isocysteine-,
(amino acid)$^1$-(amino acid)$^2$-homocysteine-,
(amino acid)$^1$-(amino acid)$^2$-penicillamine-,
(amino acid)$^1$-(amino acid)$^2$-2-mercaptoethylamine-,
(amino acid)$^1$-(amino acid)$^2$-2-mercaptopropylamine-, (amino acid)¹-(amino acid)²-2-mercapto-2-methylpropylamine-, (amino acid)¹-(amino acid)²-3-mercaptopropylamine-, wherein (amino acid) in a primary α- or β-amino acid not comprising a thiol group and wherein the chelator is attached to either a targeting moiety or a linker group via a covalent bond with the carboxyl terminus of the chelator or a side chain on one of the amino acid groups.

Most preferred chelators also include chelators of the above formula wherein (amino acid)¹ is either an α,ω- or β,ω-amino acid wherein the α- or β-amino group is a free amine and the α,ω- or β,ω-amino acid is covalently linked via the ω amino group.

Other most preferred chelators include those selected from the group consisting of:

—cysteine-(amino acid)-(α,β- or β,γ-diamino acid);
—isocysteine-(amino acid)-(α,β- or β,γ-diamino acid);
—homocysteine-(amino acid)-(α,β- or β,γ-diamino acid);
—penicillamine-(amino acid)-(α,β- or β,γ-diamino acid);
2-mercaptoacetic acid-(amino acid)-(α,β- or β,γ-diamino acid);
2- or 3-mercaptopropionic acid-(amino acid)-(α,β- or β,γ-diamino acid);
2-mercapto-2-methylpropionic acid-(amino acid)-(α,β- or β,γ-diamino acid);

wherein (amino acid) in a primary α- or β-amino acid not comprising a thiol group and wherein the chelator is attached to either a targeting moiety or a linker group via a covalent bond with the amino terminus of the chelator or a side chain on one of the amino acid groups.

Particularly preferred metal chelators are selected from the group consisting of: Gly-Gly-Cys-, Arg-Gly-Cys-, -(ε-Lys)-Gly-Cys-, -(δ-Orn)-Gly-Cys-, -(γ-Dab)-Gly-Cys-, and -(β-Dap)-Gly-Cys-. (In these formulae, it will be understood that: ε-Lys represents a lysine residue in which the ε-amino group, rather than the typical α-amino group, is covalently linked to the carboxyl group of the adjacent amino acid to form a peptide bond; δ-Orn represents an ornithine residue in which the δ-amino group, rather than the typical α-amino group, is covalently linked to the carboxyl group of the adjacent amino acid to form a peptide bond; γ-Dab represents a 2,4-diaminobutyric acid residue in which the γ-amino group is covalently linked to the carboxyl group of the adjacent amino acid to form a peptide bond; and β-Dap represents a 1,3-diaminopropionic acid residue in which the β-amino group is covalently linked to the carboxyl group of the adjacent amino acid to form a peptide bond.)

An example of preferred chelating moieties of structure type (III) above is the chelator Gly-Gly-Cys- which forms a chelating moiety having the structure:

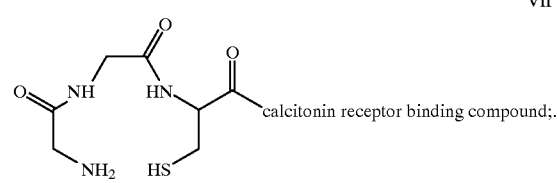

VII

Chelating ligands having structure type VII form oxo-technetiun complexes having the structure:

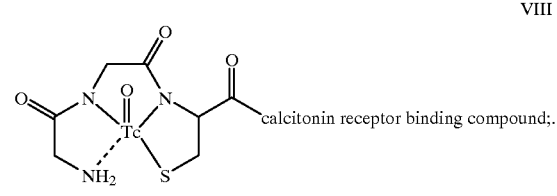

VIII

An example of more preferred chelating moieties having structure type V as shown above is Lys-(ω-peptide)-Gly-Cys.amide which forms a chelating moiety of structure:

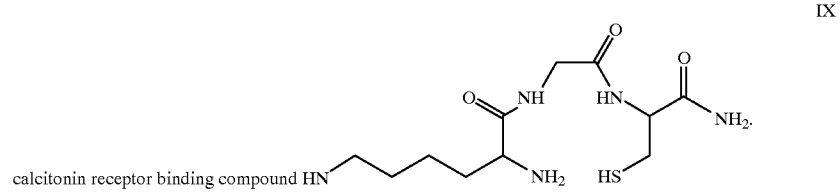

IX

Chelating ligands having structure type IX form oxotechnetium complexes having the structure:

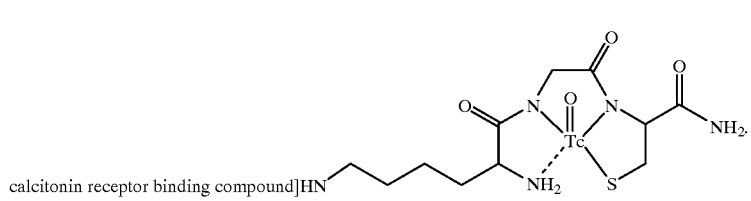

X

An example of a reagent for preparing a radiopharmaceutical agent as provided by this invention comprising a chelating moiety having structure type II as shown above is (targeting moiety)-Cys-Gly-α,β-diaminopropionamide which forms a chelating moiety of structure:

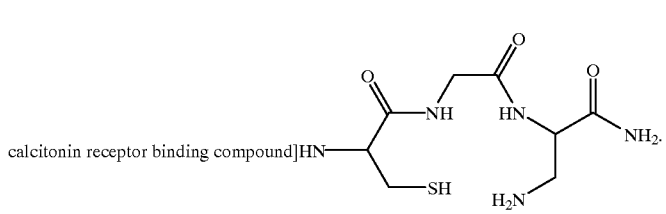

XI

Radiodiagnostic agents having structure type XI form oxotechnetium complexes having the structure:

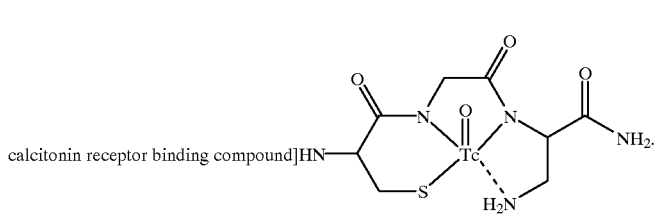

XII

This invention also provides methods for preparing peptide-comprising embodiments of the reagents of the invention by chemical synthesis in vitro. In a preferred embodiment, calcitonin receptor binding peptides are synthesized by solid phase peptide synthesis.

This invention provides reagents for preparing a radiolabeled calcitonin receptor-binding agent comprising the calcitonin receptor-binding compounds, preferably peptides, of the invention covalently linked to a chelating moiety. In a preferred embodiment, the reagent is radioactively labeled with Tc-99m. In another preferred embodiment, the reagent is radioactively labeled with $^{186}$Re or $^{188}$Re.

The invention also comprises agents that are complexes of the calcitonin receptor-binding compounds, preferably peptides, of the invention with a radioisotope, as well as methods for radiolabeling the reagents of the invention. For example, scintigraphic imaging agents provided by the invention comprise Tc-99m labeled complexes formed by reacting the reagents of the invention with Tc-99m in the presence of a reducing agent. Preferred reducing agents include but are not limited to dithionite ion, stannous ion and ferrous ion. Such Tc-99m complexes of the invention are also formed by labeling the reagents of the invention with Tc-99m by ligand exchange of a prereduced Tc-99m complex as provided herein.

The invention also provides kits for preparing radiolabeled calcitonin receptor binding compounds from the reagents of the invention. Kits for radiolabeling the reagents of the invention are comprised of a sealed vial containing a predetermined quantity of a reagent of the invention and a sufficient amount of reducing agent to radiolabel the reagent. In one aspect of preferred embodiments of the kits of the invention are kits for radiolabeling the reagents of the invention with Tc-99m. Kits for preparing radiotherapeutic agents are also provided, wherein the preferred radioisotopes are rhenium-186 and rhenium-188.

This invention provides methods for using the radiolabeled calcitonin receptor-binding compounds, preferably peptides, of the invention diagnostically and therapeutically. In one embodiment of the invention, methods are provided for using scintigraphic imaging agents that are Tc-99m labeled peptides for imaging sites within a mammalian body by obtaining in vivo gamma scintigraphic images. These methods comprise administering an effective diagnostic amount of radiolabeled peptides of the invention and detecting the gamma radiation emitted by the radiolabel localized at the site within the mammalian body.

The invention also provides methods for alleviating calcitonin-related diseases in animals, preferably humans, comprising administering a therapeutically effective amount of the radiolabeled calcitonin receptor-binding compound, preferably peptide, reagents of the invention to the animal. In preferred embodiments, the reagent is radioactively labeled with $^{186}$Re or $^{188}$Re.

This invention also provides calcitonin receptor-binding compounds, preferably peptides, that are covalently linked to a metal-binding moiety and that are complexed with a magnetic, paramagnetic, supermagnetic, or superparamagnetic metal atom, ion or particle, and methods for using such complexes for magnetic-based detection of localization of such calcitonin receptor binding peptide complexes at tumor or other tissue sites in vivo. Thus, the invention provides non-radioactive methods for localizing tumor and other calcitonin receptor expressing tissues in vivo.

The calcitonin receptor binding compounds and calcitonin receptor binding reagents of the invention may also be comprised of a polyvalent linking moiety. Polyvalent linking moieties of the invention are comprised of at least 2 identical linker functional groups capable of covalently bonding to calcitonin analogues, calcitonin receptor binding compounds, calcitonin peptides or chelating moieties or both. Preferred linker functional groups are primary or secondary amines, hydroxyl groups, carboxylic acid groups or thiol-reactive groups. In preferred embodiments, the polyvalent linking moieties are comprised of bis-succinimidylmethylether (BSME), bis-succinimidyl-ethylether (BSEE), 4-(2,2-dimethylacetyl)benzoic acid (DMBA), N-{2-(N',N'-bis(2-succinimido-ethyl)aminoethyl)}-N$^6$,N$^9$-bis(2-methyl-2-mercapto-propyl)-6,9-diazanonanamide (BAT-BS), tris(succinimidylethyl)amine (TSEA), bis-succinimidohexane (BSH), 4-(O-CH$_2$CO-Gly-Gly-Cys.amide)-2-methylpropiophenone (ETAC), tris-(acetamidoethyl)amine, bis-acetamidomethyl ether, bis-acetamidoethyl ether, α,ε-bis-acetyllysine, lysine and 1,8-bis-acetamido-3,6-dioxa-octane, or derivatives thereof.

Specific preferred embodiments of the present invention will become evident from the following more detailed description of certain preferred embodiments and the claims.

DETAILED DESCRIPTION OF THE INVENTION

Figure 1:
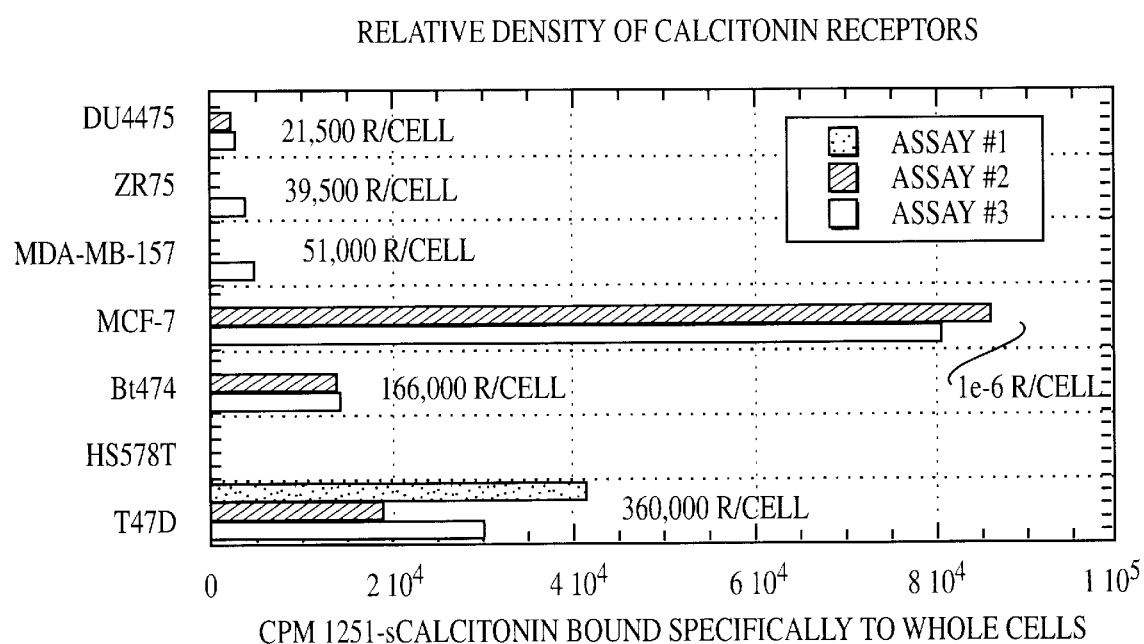

The present invention provides calcitonin receptor binding compounds having a molecular weight of 10,000 daltons or less, wherein the compounds of the invention preferably comprise peptides and most preferably calcitonin peptides, derivatives and analogues thereof that are useful as reagents in the preparation of calcitonin receptor binding radiopharmaceutical agents for diagnosis and therapy.

Embodiments of these calcitonin receptor binding provided by this invention are calcitonin receptor binding peptide reagents wherein the calcitonin receptor binding peptides, derivatives and analogues thereof are covalently linked to a chelating moiety. Such calcitonin receptor binding peptide reagents are capable of being radiolabeled to provide radiodiagnostic or radiotherapeutic agents. One example of a radiodiagnostic application using the radiolabeled agents of the invention is scintigraphic imaging, wherein the location and extent of calcitonin receptor-bearing tumors may be determined. The calcitonin receptor binding reagents of the invention can also advantageously be radiolabeled with cytotoxic radioisotopes such as rhenium-186 or rhenium-188 for radiotherapeutic uses.

The term scintigraphic imaging agent as used herein is meant to encompass a radiolabeled agent capable of being detected with a radioactivity detecting means (including but not limited to a gamma-camera or a scintillation detector probe).

Radiotherapeutic embodiments of the invention, on the other hand, are advantageously labeled with rhenium-186 and rhenium-188. Such embodiments are useful in the treatment of calcitonin-related diseases or other ailments in animals, preferably humans, including but not limited to breast cancer, ovarian cancer, lung cancer, lymphoma and other diseases characterized by the growth of malignant or benign tumors capable of binding calcitonin receptor binding compounds, calcitonin or derivatives or analogues thereof via the expression of calcitonin receptors on the cell surface of cells comprising such tumors.

For the purposes of this invention, the term "calcitonin receptor binding affinity" is intended to mean binding affinity as measured by any methods known to those of skill in the art, including, inter alia, those methods which measure binding affinity by a dissociation constant, an inhibition constant or an IC$_{50}$ value. The term "having an affinity of at least one-tenth the affinity of radioiodinated calcitonin" is intended to mean that the affinity is not less than ten times less than the affinity of radioiodinated calcitonin, or that the inhibition constant (K$_i$) or IC$_{50}$ is not more than 10 times that of radioiodinated calcitonin. The term "having a CTR binding affinity equal to or greater than native calcitonin or radioiodinated species thereof" is intended to encompass reagents as disclosed herein wherein the affinity is equal to or greater than the affinity of native calcitonin or radioiodinated calcitonin, or the inhibition constant (K$_i$) or IC$_{50}$ is equal to or less than that of calcitonin or radioiodinated calcitonin In the chelating moieties and calcitonin receptor binding compounds covalently linked to such moieties that contain a thiol covalently linked to a thiol protecting group {(pgp)$^S$} provided by the invention, the thiol-protecting groups may be the same or different and may be but are not limited to:

—CH$_2$-aryl (aryl is phenyl or alkyl or alkyloxy substituted phenyl);
—CH-(aryl)$_2$, (aryl is phenyl or alkyl or alkyloxy substituted phenyl);
—C-(aryl)$_3$, (aryl is phenyl or alkyl or alkyloxy substituted phenyl);
—CH$_2$-(4-methoxyphenyl);
—CH-(4-pyridyl)(phenyl)$_2$;
—C(CH$_3$)$_3$—9-phenylfluorenyl;
—CH$_2$NHCOR (R is unsubstituted or substituted alkyl or aryl);
—CH$_2$-NHCOOR (R is unsubstituted or substituted alkyl or aryl);
—CONHR (R is unsubstituted or substituted alkyl or aryl);
—CH$_2$—S—CH$_2$-phenyl Preferred protecting groups have the formula —CH$_2$—NHCOR wherein R is a lower alkyl having 1 and 8 carbon atoms, phenyl or phenyl-substituted with lower alkyl, hydroxyl, lower alkoxy, carboxy, or lower alkoxycarbonyl. The most preferred protecting group is an acetamidomethyl group.

For the purposes of this invention, the term "calcitonin receptor binding compound" is intended to encompass naturally-occurring calcitonin, fragments, analogues and derivatives thereof that specifically bind to the calcitonin receptor expressed in a variety of cell types recognized by those with skill in the art, and compounds having a molecular weight of 10,000 daltons or less that specifically bind to calcitonin receptors. Compounds designed to mimic the receptor-binding properties of calcitonin are also included in this definition and encompassed by the invention.

Calcitonin receptor binding peptides comprising the reagents of the invention include naturally-occurring human calcitonin, and peptidomimetics including:

CH$_2$CO.SNLST.Hhc.VLGKLSCELHKLQTYPRTNTG-SGTP.amide (SEQ ID No. 5),

CH$_2$CO.SNLST.Hcy.VLGKLSCELHKLQTYPRTNTG-SGTP.amide (SEQ ID No. 6),

CH$_2$CO.SNLST.Cys.VLGKLSCELHKLQTYPRTNTG-SGTP.amide (SEQ ID No. 7), and

SNLST.Asu.VLGKLSCELHKLQTYPRT-NTGSGTP.amide (SEQ ID No. 8).

Particularly preferred embodiments of the reagents of the invention include:

CH$_2$CO.SNLST.Hhc.VLGKLSC(BAT)ELHKLQTYPR-TNTGSGTP.amide (SEQ ID No. 4),

CH$_2$CO.SNLST.Hhc.VLGKLSQELHKLQTYPRTNT-GSGTP(ε-K)GC.amide,

CH$_2$CO.SNLST.Hhc.VLGKLSC(CH$_2$CO.GGCK.amide) ELHKLQTYPRTNTGSGTP.amide,

CH$_2$CO.SNLST.Hhc.VLGKLSC(CH$_2$CO.(β-Dap)KCK. amide)ELHKLQTYPRTNTGSGTP.amide,

CH$_2$CO.SNLST.Hhc.VLGKLSC(CH$_2$CO.(ε-K)GCE. amide)ELHKLQTYPRTNTGSGTP.amide,

CH$_2$CO.SNLST.Hcy.VLGKLSC(CH$_2$CO.GGCK.amide)
ELHKLQTYPRTNTGSGT.amide,
CH$_2$CO.SNLST.Hcy.VLGKLSC(CH$_2$CO.(β-Dap)KCK.
amide)ELHKLQTYPRTNTGSGTP.amide,
CH$_2$CO.SNLST.Hcy.VLGKLSC(CH$_2$CO.(ε-K)GCE.
amide)ELHKLQTYPRTNTGSGTP.amide,
CH$_2$CO.SNLST.Cys.VLGKLSC(CH$_2$CO.GGCK.amide)
ELHKLQTYPRTNTGSGTP.amide,
CH$_2$CO.SNLST.Cys.VLGKLSC(CH$_2$CO.(β-Dap)KCK.
amide)ELHKLQTYPRTNTGSGTP.amide,
CH$_2$CO.SNLST.Cys.VLGKLSC(CH$_2$CO.(ε-K)GCE.
amide)ELHKLQTYPRTNTGSGTP.amide,
SNLST.Asu.VLGKLSC(CH$_2$CO.(β-Dap)KCK.amide)
ELHKLQTYPRTNTGSGTP.amide, and
SNLST.Asu.VLGKLSC(CH$_2$CO.(β-Dap)KCK.amide)
ELHKLQTYPRTDVGAGTP.amide.

All naturally-occurring amino acids are abbreviated using standard abbreviations (which can be found in G. Zubay, *Biochemistry* (2d. ed.), 1988 (MacMillen Publishing: New York) p.33). For the purposes of this invention, the naturally-occurring amino acids are characterized as lipophilic (alanine, isoleucine, leucine, methionine, phenylalanine, tyrosine, proline, tryptophan and valine, as well as S-alkylated derivatives of cysteine), hydrophilic (asparagine, glutamine, threonine, serine), acidic (glutamic acid and aspartic acid), basic (arginine, histidine and lysine). ε-K is intended to represent a covalent linkage via the ε-amino group on the sidechain of a lysine residue. ε-Orn represents an ornithine residue in which the ε-amino group, rather than the typical α-amino group, is covalently linked to the carboxyl group of the adjacent amino acid to form a peptide bond. γ-Dab represents a 2,4-diaminobutyric acid residue in which the γ-amino group is covalently linked to the carboxyl group of the adjacent amino acid to form a peptide bond. β-Dap represents a 1,3-diaminopropionic acid residue in which the β-amino group is covalently linked to the carboxyl group of the adjacent amino acid to form a peptide bond. (BAT) represents N$^6$,N$^9$-bis(2-mercapto-2-methyl-propyl)-6,9-diazanonanoic acid; K.(BAT) and Lys. (BAT) represent the amino acid lysine, acylated at the ε-amino group on the amino acid sidechain to (BAT); C(BAT) and Cys(BAT) represent S-(N$^6$,N$^9$-bis(2-mercapto-2-methylpropyl)-6,9-diazanonan-1-yl)cystene; (BAM) is (N$^1$,N$^4$-bis(2-mercapto-2-methylpropyl)-1,4,10-triazadecane; (BAT-BM) is N-{2-(N',N'-bis(2-maleimidoethyl)aminoethyl }-N$^9$-(t-butoxy-carbonyl)-N$^6$, N$^9$-bis(2-methyl-2-triphenyl-methylthiopropyl)-(BAT-BS) is N-{2-(N',N'-bis(2sucinimidoethyl)aminoethyl)-N$^6$,N$^9$-bis (2-mercapto-2-methylpropyl)-6,9diazanonanamide; (BMH) is bis-maleimidohexane; (BSH) is bis-succinimidohexane; (BMME) is bis-maleimidomethylether; (BSEE) is bis-succinimidoethylether; (BMEE) is bis-maleimidoethyl-ether; and (BSME) is bis-succinimidomethylether. As used herein, the following amino acids and amino acid analogues are intended to be represented by the following abbreviations: Acm is the sulfhydryl protecting group acetamidom-ethyl; Pen is penicillamine; Aca is 6-aminocaproic acid; Hly is homolysine; Apc is L-{S-(3-aminopropyl)cysteine; F$_D$ is D-phenylalanine; W$_D$ is D-tryptophan; Y$_D$ is D-tyrosine; Cpa is L-(4-chlorophenyl)alanine; Thp is 4-amino-tetrahydrothio-pyran-4-carboxylic acid; D-Nal is D-2-naphthylalanine; Dpg is dipropylglycine; Nle is norleucine; Hcy is homocysteine; Hhc is homohomocysteine; Aib is aminoisobutyric acid; Nal is 2-naphthylalanine; D-Nal is D-2-naphthylalanine; Ain is 2-aminoindan-2-carboxylic acid; Achxa is 4-amino-cyclo-hexylalanine; Amf is 4-aminomethyl-phenylalanine; Aec is S-(2-amino ethyl) cysteine; Apc is S-(3-aminopropyl)cysteine; Aes is O-(2-aminoethyl)serine; Aps is O-(3-amino-propyl)serine; Abu is 2-aminobutyric acid; Nva is norvaline; and Asu is 2-amino suberic acid, wherein the amino terminal amino acids of peptides containing an Asu residue are cyclized via an amide bond between the amino terminal amino group and the side chain carboxylic acid moiety of the Asu residue.

Calcitonin receptor binding peptides and derivatives and analogues thereof provided by the present invention can be chemically synthesized in vitro. Peptides of the present invention can generally advantageously be prepared on a peptide synthesizer. The peptides of this invention are synthesized wherein the chelating moiety is covalently linked to the peptide during chemical synthesis in vitro, using techniques well known to those with skill in the art. Such peptides covalently-linked to the chelating moiety during synthesis are advantageous because specific sites of covalent linkage can be determined.

Chelating moieties of the invention are introduced into the target calcitonin receptor binding peptide, derivative or analog during peptide synthesis. This invention provides for the incorporation of chelating moieties in a site-selective fashion into virtually any position in the peptide. The invention in particular provides amino acid derivatives comprising radiolabel chelating moieties linked to an amino acid sidechain, wherein the chelator is incorporated into the peptide during in vitro peptide synthesis at a specific position in the peptide. The invention also provides peptides wherein the radiolabel chelating moieties are incorporated into the peptide at the carboxyl terminus. In preferred embodiments, the radiolabel chelating moiety is incorporated into a sidechain of an amino acid of the calcitonin receptor binding peptide, wherein the amino acid is an amino acid in the sequence CH$_2$CO.SNLST.Hhc.VLGKLSCELHKLQTYPRTNTG-SGTP.amide (SEQ ID No. 5) of the peptide. In preferred embodiments, the radiolabel chelating moiety is incorporated into the synthetic, calcitonin receptor binding peptide at the sidechain sulfur atom of the cysteine amino acid at position 14 or the native peptide, and position 13 of the peptidomimetic peptides of the invention (distinguished by the bold highlighting in the peptide above).

In yet further preferred embodiments, the radiolabel chelating moiety is incorporated into the synthetic, calcitonin receptor binding peptide at the carboxyl terminus of the peptide.

The invention encompasses reagents whereby the radiometal chelating group is incorporated into the peptide during peptide synthesis, most preferably during solid phase peptide synthesis. In particular, the CTR binding peptides of the invention are preferably prepared having a protected thiol-containing amino acid, typically a cysteine residue, incorporated into the peptide. Following cleavage of the peptide from the synthetic resin and cyclization of the amino terminal residues, the protected thiol group is deprotected and elaborated with a prosthetic group containing a radiometal binding moiety and a thiol-reactive group. It is a particular advantage of the reagents of the invention that they are provided having the radiolabel chelating moiety incorporated into the peptide during synthesis. This is advantageous because it allows placement of the chelator at a known position in calcitonin, or in a calcitonin fragment, analogue or derivative so as to avoid decreasing the affinity of the peptide for the calcitonin receptor. In contrast with the presently provided methods, methods for introducing chelators into peptides that were described in the prior art are disadvantageous for use with peptides, since these methods have generally been developed from methods first developed for conjugating chelators with proteins, which, being much larger than peptides, are not as sensitive to the effects of non-site-specific introduction of the chelating moiety. Peptides produced using prior art methods are disadvantageous as compared with the site-specific introduction of the chelators in the peptides of this invention due to the likelihood of introducing the chelator in such a way as to decrease peptide binding affinity, when using the methods of the prior art.

It is also an advantage of this invention that the peptides are provided as chemically-synthesized peptides. This is because chemical synthesis is a controlled process amenable to chemical engineering techniques that are capable of providing a quality-controlled and pharmaceutically-suitable product. Chemical synthesis methods are preferred over other methods, such as biological synthesis and extraction, which may involve the introduction of pathogens (viruses, mycoplasma, etc.) which require costly measures to remove or prove absent. Products prepared by chemical synthesis are less expensive to produce and more amenable to successful regulatory approval, thereby impacting the ability to bring pharmaceutical embodiments into the clinic and to market expeditiously.

In forming a complex of radioactive technetium or rhenium with the reagents of this invention, the technetium complex, preferably a salt of Tc-99m pertechnetate, or rhenium in the form of perrhenate, is reacted with the reagent in the presence of a reducing agent. Preferred reducing agents are dithionite, stannous and ferrous ions; the most preferred reducing agent is stannous chloride. Means for preparing such complexes are conveniently provided in a kit form comprising a sealed vial containing a predetermined quantity of a reagent of the invention to be labeled and a sufficient amount of reducing agent to label the reagent with Tc-99m, Re-186 or Re-188. Alternatively, the complex may be formed by reacting a reagent of this invention with a pre-formed labile complex of technetium or rhenium and another compound known as a transfer ligand. This process is known as ligand exchange and is well known to those skilled in the art. The labile complex may be formed using such transfer ligands as tartrate, citrate, gluconate or mannitol, for example. Among the Tc-99m pertechnetate and rhenium salts useful with the present invention are included the alkali metal salts such as the sodium salt, or ammonium salts or lower alkyl ammonium salts.

In a preferred embodiment of the invention, a kit for preparing technetium- or rhenium-labeled peptides is provided. An appropriate amount of a reagent of the invention is introduced into a vial containing a reducing agent, such as stannous chloride, in an amount sufficient to label the reagent with Tc-99m, Re-186 or Re-188. An appropriate amount of a transfer ligand as described (such as tartrate, citrate, gluconate, glucoheptanate or mannitol, for example) can also be included. The kit may also contain conventional pharmaceutical adjunct materials such as, for example, pharmaceutically acceptable salts to adjust the osmotic pressure, buffers, preservatives and the like. The components of the kit may be in liquid, frozen or dry form. In a preferred embodiment, kit components are provided in lyophilized form.

Tc-99m, Re-186 and Re-188 labeled radiopharmaceuticals according to the present invention may be prepared by the addition of an appropriate amount of Tc-99m, Re-186 or Re-188, or radionuclide complexes thereof, into the vials and reaction under conditions described in the Examples below.

The invention also provides methods of using calcitonin receptor binding compounds, including calcitonin itself, calcitonin derivatives and calcitonin analogues radiolabeled with iodine radioisotopes, including I-123 and I-131, preferably I-123, wherein peptide embodiments are radioiodinated at a tyrosine residue in the peptide, either as naturally-occurring or added at a position in the peptide that does not disrupt binding of the peptide to calcitonin receptors. Radio- iodinated mimetics and peptidomimetics, as well as other small molecules that specifically bind to the calcitonin receptor, are also provided by the invention. Dose, sites and routes of administration, formulations and administered specific radioactivity of such embodiments are as described herein for technetium and rhenium-labeled reagents for scintigraphic and therapeutic uses.

Radioactively-labeled scintigraphic imaging agents provided by the present invention are provided having a suitable amount of radioactivity. In forming Tc-99m, Re-186 or Re-188 radioactive complexes, it is generally preferred to form radioactive complexes in solutions containing radioactivity at concentrations of from about 0.01 millicurie (mCi) to 100 mCi per mL.

The imaging reagents provided by the present invention can be used for visualizing sites of expression or hyperexpression of calcitonin receptors, including organs such as the kidney or bone for diagnosing disorders in these organs, and tumors, in particular lung, ovarian and breast cancers, and particularly metastic cells and tumors thereof, that can be imaged. In accordance with this invention, for scintigraphic imaging the Tc-99m labeled reagents of the invention are administered in a single unit injectable dose. The Tc-99m labeled reagents provided by the invention may be administered intravenously in any conventional medium for intravenous injection such as an aqueous saline medium, or in blood plasma medium. Generally, the unit dose to be administered has a radioactivity of about 0.01 mCi to about 100 mCi, preferably 1 mCi to 20 mCi. The solution to be injected at unit dosage is from about 0.01 mL to about 10 mL. After intravenous administration, imaging in vivo can take place in a matter of a few minutes. However, imaging can take place, if desired, in hours or even longer, after the radiolabeled reagent is injected into a patient. In most instances, a sufficient amount of the administered dose will accumulate in the area to be imaged within about 0.1 of an hour to permit the taking of scintiphotos. Any conventional method of scintigraphic imaging for diagnostic purposes can be utilized in accordance with this invention.

This invention also provides peptides radiolabeled with cytotoxic radioisotopes such as rhenium-186 or rhenium-188 that may be used for radiotherapy of certain tumors as described above. For this purpose, an amount of radioactive isotope from about 10 mCi to about 200 mCi may be administered via any suitable clinical route, preferably by intravenous injection.

This invention also provides calcitonin receptor-binding compounds, preferably peptides, covalently linked to a metal-binding moiety that are complexed with a magnetic, paramagnetic, supermagnetic, or superparamagnetic metal atom, ion or particle, and methods for using such complexes for magnetic-based detection of localization of such calcitonin receptor binding complexes at tumor or other tissue sites in vivo. Thus, the invention provides non-radioactive methods for localizing tumor and other calcitonin receptor expressing tissues in vivo.

This invention provides methods for using the diagnostic, radiodiagnostic, therapeutic and radiotherapeutic agents of the invention. For radiolabeled embodiments of the agents of the invention, for example, Tc-99m labeled scintigraphic imaging agents, an effective diagnostic or therapeutic amount of the diagnostic, radiodiagnostic, therapeutic or radiotherapeutic agent of the invention are administered. In radiodiagnostic embodiments, localization of the radiolabel is detected using conventional methodologies such as gamma scintigraphy. In non-radioactive diagnostic embodiments, localization of sites of accumulation of the paramagnetic metal-labeled diagnostic agents of the invention is achieved using magnetic resonance imaging methodologies. For the purposes of this invention, radiotherapy is defined as a therapeutic effect ranging from pain palliation to cure.

The imaging agents provided by the invention have utility for tumor imaging, particularly for imaging primary and metastatic neoplastic sites wherein said neoplastic cells express calcitonin receptors, and in particular such primary and especially metastatic breast, lung and ovarian tumor-derived cells that have been clinically recalcitrant to detection using conventional methodologies.

Those having skill in this art will recognize that efficacious radiopharmaceuticals can be identified, tested and characterized using any of a number of in vitro methodologies known in the art. Such methodologies include, inter alia, the determination of dissociation constants or inhibition constants of binding of the radiopharmaceuticals of the invention to their cognate calcitonin receptors, as well as comparison of the affinity or avidity of such binding with binding of radiolabeled, for example, $^{125}$I-labeled calcitonin itself, and in experiments wherein a radiopharmaceutical of the invention is used in competition with radiolabeled calcitonin, or in the converse experiments using unlabeled calcitonin in competition with radiopharmaceutical of the invention.

In the practice of this invention, effective radiodiagnostic and radiotherapeutic agents are prepared as follows. Reagents of the invention comprising calcitonin receptor binding, and calcitonin fragments, analogues and derivatives thereof, are synthesized using the methods of the invention wherein the chelating moiety is incorporated into the peptide during synthesis. The reagents of the invention are then complexed with rhenium, preferably as ReO, as further disclosed herein. Calcitonin receptor binding is then evaluated in in vitro competition binding assays as described herein using radioiodinated calcitonin, as disclosed in Example 4 below.

The methods for making and labeling these compounds are more fully illustrated in the following Examples. These Examples illustrate certain aspects of the above-described method and advantageous results, and are shown by way of illustration and not limitation.

EXAMPLE 1

Synthesis of BAT Chelators

BAT chelators, in particular S-cysteine derived and ε-amino Lysine derived BAT chelators, are prepared according to the methods of co-owned and co-pending U.S. Ser. No. 08/414,424 now U.S. Pat. No. 5,849,261, incorporated by reference herein.

EXAMPLE 2

Solid Phase Peptide Synthesis

Solid phase peptide synthesis (SPPS) was carried out on a 0.25 millimole (mmole) scale using an Applied Biosystems Model 431A Peptide Synthesizer and using 9-fluorenylmethyloxy-carbonyl (Fmoc) amino-terminus protection, coupling with dicyclohexylcarbodiimide/hydroxy-benzotriazole or 2-(1H-benzotriazol-1-yl)-1,1,3,3-tetramethyluronium hexafluorophosphate/hydroxybenzotriazole (HBTU/HOBT), and using p-hydroxymethyl phenoxymethyl-polystyrene (HMP) resin or Sasrin™ or chlorotrityl resin for carboxyl-terminus acids or Rink amide resin for carboxyl-terminus amides.

Where appropriate, Fmoc-Cys(BAT) and Nα-Fmoc-Nε-(BAT)Lys were synthesized as described in co-owned and co-pending U.S. Ser. No. 08/414,424, now U.S. Pat. No. 5,849,261 incorporated by reference herein.

Where appropriate, 2-chloroacetyl, 2-bromoacetyl and 2-bromo-3-phenylpropionyl groups are introduced either by using the appropriate 2-halo acid as the last residue coupled during SPPS, or by treating the N-terminus free amino acid peptide bound to the resin with either 2-halo acid/diisopropylcarbodiimide/N-hydroxysuccinimide/NMP or 2-halo acid anhydride/diisopropylethylamine/NMP.

Where appropriate, HPLC-purified 2-haloacylated peptides are cyclized by stirring an 0.1–1.0 mg/mL solution in phosphate or bicarbonate buffer or dilute ammonium hydroxide (pH 8.0), optionally containing 0.5–1.0 mM EDTA, or acetonitrile or THF for 1–48 h followed optionally by acidification with acetic acid, lyophilization and HPLC purification.

Where appropriate, thiol-containing peptides are reacted with chloroacetyl-containing, thiol-protected Tc-99m complexing moieties at pH 10 for 0.5–4 hours at room temperature, followed by acetic acid acidification and evaporation of the solution to give the corresponding peptide-sulfide adduct. Deprotection and purification are routinely performed as described to yield the chelator-peptide conjugate.

Where appropriate, BSME, BSEE and BSH adducts are prepared by reacting single thiol-containing peptides (5 to 50 mg/mL in DMF buffered to pH 7 with N-methylmorpholine or N-ethyl-morpholine, or 50 mM sodium phosphate buffer, pH 7–8, optionally containing 0.5 mM EDTA or DMF or THF or acetonitrile) with 0.5 molar equivalents of BMME (bis-maleimidomethylether), BMEE (bis-maleimidoethylether) or BMH (bis-maleimidohexane), respectively, pre-dissolved in acetonitrile at room temperature for approximately 1–18 hours. The solution was concentrated and the product was purified by HPLC.

Where appropriate, TSEA adducts are prepared by reacting single thiol-containing peptide (at concentrations of 10 to 100 mg/mL peptide in DMF buffered to pH 7 with N-methylmorpholine or N-ethylmorpholine, or 5 to 50 mg/mL peptide in 50 mM sodium phosphate, pH 7–8, optionally containing 0.5 mM EDTA or DMF or THF or acetonitrile) with 0.33 molar equivalents of TMEA (tris(2-maleimidoethyl)amine) pre-dissolved in acetonitrile or DMF, with or without 1 molar equivalent of triethanolamine, at room temperature for approximately 1–18 h. Such reaction mixtures containing adducts are concentrated and the adducts are then purified using HPLC.

Where appropriate, (BAM) ($N^1,N^4$-bis(2-mercapto-2-methylpropyl)-1,4,10-triazadecane) is conjugated to the peptide by first activating the peptide carboxylate with a mixture of diisopropylcarbodiimide/N-hydroxysuccinimide or HBTU/HOBt in DMF, NMP or methylene chloride, followed by coupling in the presence of diisopropylethylamine. After coupling, the conjugates are deprotected as described above.

Where appropriate, (BAT) ($N^6,N^9$-bis(2-mercapto-2-methylpropyl)-6,9-diazanonanoic acid) is incorporated into peptides as protected amino acid derivatives, such as (Nα (Fmoc)-Nε(N-Boc)-S,S'-bistrityl-BAT)lysine (prepared from Nα(Fmoc)-lysine and Nε(N-Boc)-S,S'-bistrityl-BAT as described in Example 2 of co-owned and U.S. patent application Ser. No. 08/044,825 U.S. Pat. No. 5,645,815, incorporated by reference), or as (N(Fmoc)-S,S'-bistrityl-BAT)cysteine (prepared as described in Example 1F of co-owned and copending U.S. Ser. No.8/414,424 now U.S. Pat. No. 5,849,261, incorporated by reference) during peptide synthesis and then deprotected after cleavage of the completed peptide from the synthetic resin.

Where appropriate, BAT-BS (N-{2-(N',N'-bis(2-succinimidoethyl) aminoethyl)}-$N^6$,$N^9$-bis(2-methyl-2-mercaptopropyl)-6,9-diazanonanamide) adducts are prepared by reacting single thiol-containing peptide (at concentrations of 2 to 50 mg/mL peptide in DMF buffered to pH 7 with N-methylmorpholine or N-ethylmorpholine, or in 50 mM sodium phosphate (pH 7–8), optionally containing 0.5 mM EDTA or DMF or THF or acetonitrile) with 0.5 molar equivalents of BAT-BM (N-{2-(N'N'-bis(2-maleimidoethyl)aminoethyl)}-$N^9$-(t-butoxycarbonyl)-$N^6$, $N^9$-bis(2-methyl-2-triphenylmethylthiopropyl)-6,9-diazanonanamide) pre-dissolved in acetonitrile or THF, at room temperature for approximately 1–18 h. The solution is then evaporated to dryness and (BAT-BS)-peptide conjugates deprotected by treatment with 10 mL TFA and 0.2 mL triethylsilane for 1 h. The solution is concentrated, the product adducts precipitated with ether, and then purified by HPLC.

Where appropriate, peptide precursors are cyclized (between the amino- and carboxyl-termini) by reaction of the sidechain-protected, N-terminal free amine and C-terminal free acid with diphenylphosphorylazide.

Sasrin™ resin-bound peptides are cleaved using a solution of 1% TFA in dichloromethane to yield the protected peptide. Where appropriate, protected peptide precursors are cyclized between the amino- and carboxyl-termini by reaction of sidechain-protected, amino-terminal free amine and carboxyl-terminal free acid using diphenylphosphorylazide.

HMP or Rink amide resin-bound products are routinely cleaved and protected cyclized peptides deprotected using a solution comprised of trifluoroacetic acid (TFA), or TFA and methylene chloride, optionally comprising water, thioanisole, ethanedithiol, and triethylsilane or triisopropylsilane in ratios of 100:5:5:2.5:2, for 0.5–3 hours at room temperature. Where appropriate, products were re-S-tritylated in triphenolmethanol/TFA, and N-Boc groups re-introduced into the peptide using $(Boc)_2O$.

Where appropriate, thiol functionalities within the peptide or peptidometic sequence designed for further elaboration with a prosthetic group were protected using compound such as S-t-butyl (to produce mixed t-butyl disulfides) or p-methoxybenzyl. S-t-butyl groups are removed by treatment with a solution of dithiothreitol or mercaptoethanol, while p-methoxybenzyl groups are removed using boron trifluoride etherate in trifluoroacetic acid in the presence of a free radical scavenger such as m-cresol. Prosthetic peptides containing radiometal binding moieties are prepared by SPPS ending with an N-terminal 2-haloacetyl group. The prosthetic group are removed from the resin and any thiol groups are-protected, for example, with a trityl group. The haloacetylated sequence is then coupled with the thiol-containing peptide under essentially the same conditions as described above for preparing cyclic thioethers. Removal of remaining protecting groups is then achieved using the methods described herein to yield the final product.

Crude peptides are purified by preparative high pressure liquid chromatography (HPLC) using a Waters Delta Pak C18 column and gradient elution using 0.1% trifluoroacetic acid (TFA) in water modified with acetonitrile. Acetonitrile is evaporated from the eluted fractions which are then lyophilized. The identity of each product is confirmed by fast atom bombardment mass spectroscopy (FABMS) or by electrospray mass spectroscopy (ESMS).

Calcitonin receptor binding peptides, derivatives and analogues synthesized as provided herein, as well as the products of such synthesis identified by FABMS, are shown in Table I below.

TABLE I

| Peptide | Peptide | ReO Complex |
|---|---|---|
| $CH_2CO.SNLST.Hhc.VLGKLSC(BAT)ELHKLQTYPRTNTGSGTP.amide$ | 3679 | 3877 |
| $CH_2CO.SNLST.Hhc.VLGKLSQELHKLQTYPRTNTGSGTP(\epsilon-K)GC.amide$ | 3687 | 3886 |
| $CH_2CO.SNLST.Hhc.VLGKLSCELHKLQTYPRTNTGSGTP.amide$ | 3373 | NA |
| $CH_2CO.SNLST.Hhc.VLGKLSC(CH_2CO.GGCK.amide)ELHKLQTYPRTNTGSGTP.amide$ | 3873 | 4078 |
| $CH_2CO.SNLST.Hhc.VLGKLSC(CH_2CO.(\beta-Dap)KCK.amide)ELHKLQTYPRTNTGSGTP.amide$ | 3777 | 3975 |
| $CH_2CO.SNLST.Hhc.VLGKLSC(CH_2CO.(\epsilon-K)GCE.amide)ELHKLQTYPRTNTGSGTP.amide$ | 3849 | 4047 |
| $CH_2CO.SNLST.Hcy.VLGKLSCELHKLQTYPRTNTGSGTP.amide$ | 3360 | NA |
| $CH_2CO.SNLST.Hcy.VLGKLSC(CH_2CO.GGCK.amide)ELHKLQTYPRTNTGSGTP.amide$ | 3762 | 3962 |
| $CH_2CO.SNLST.Hcy.VLGKLSC(CH_2CO.(\beta-Dap)KCK.amide)ELHKLQTYPRTNTGSGTP.amide$ | 3862 | 4063 |
| $CH_2CO.SNLST.Hcy.VLGKLSC(CH_2CO.(\epsilon-K)GCE.amide)ELHKLQTYPRTNTGSGTP.amide$ | 3835 | 4033 |
| $CH_2CO.SNLST.Cys.VLGKLSCELHKLQTYPRTNTGSGTP.amide$ | 3346 | NA |
| $CH_2CO.SNLST.Cys.VLGKLSC(CH_2CO.GGCK.amide)ELHKLQTYPRTNTGSGTP.amide$ | 3748 | 3947 |
| $CH_2CO.SNLST.Cys.VLGKLSC(CH_2CO.(\beta-Dap)KCK.amide)ELHKLQTYPRTNTGSGTP.amide$ | 3848 | 4048 |
| $CH_2CO.SNLST.Cys.VLGKLSC(CH_2CO.(\epsilon-K)GCE.amide)ELHKLQTYPRTNTGSGTP.amide$ | 3820 | 4019 |
| SNLST.Asu.VLGKLSCELHKLQTYPRTNTGSGTP.amide | 3356 | NA |
| $SNLST.Asu.VLGKLSC(CH_2CO.(\beta-Dap)KCK.amide)ELHKLQTYPRTNTGSGTP.amide$ | 3858 | 4057 |
| SNLST.Asu.VLGKLSCELHKLQTYPRTDVGAGTP.amide | 3338 | NA |
| $SNLST.Asu.VLGKLSC(CH_2CO.(\beta-Dap)KCK.amide)ELHKLQTYPRTDVGAGTP.amide$ | 3841 | 4040 |

$M^+$ determined by electrospray mass spectrometry for: P994, P995, P1130, P1156, P1409, P1410, P1231, P1365, P1366, P1232, P1367 and P1441
$M^+$ determined by fast atom bombardment mass spectrometry for all other peptides.

EXAMPLE 3

A General Method for Radiolabeling with Tc-99m 0.1 mg of a peptide prepared as in Example 2 was dissolved in 0.1 mL or 0.2 mL of water or 0.9% saline. Tc-99m gluceptate was prepared by reconstituting a Glucoscan vial (E.I. DuPont de Nemours, Inc., Wilmington, Del.) with 0.25 mL of Tc-99m sodium pertechnetate containing up to 200 mCi and allowed to stand for 15 minutes at room temperature. 25 μl of Tc-99m gluceptate was then added to the peptide and the reaction allowed to proceed at room temperature for 15 to 60 min or at 100° C. for 10 to 30 min, and then filtered through a 0.2 μm filter.

The Tc-99m labeled peptide purity was determined by reverse-phase HPLC using the following conditions: a Waters Delta Pak C-18, 5μ, 3.9 mm×150 mm analytical column was loaded with each radiolabeled peptide, and the peptides eluted at a solvent flow rate equal to 1 mL/min (Delta-Pak). Gradient elution was performed using a gradient of 20–50% Solvent B/Solvent A (Solvent A is 0.1% $CF_3COOH$ in water and Solvent B is 0.1% $CF_3COOH$ in 90/10 $CH_3CN/H_2O$) for 20 min., followed by 100% B/A for 3 min.

Radioactive components were detected using an in-line radiometric detector linked to an integrating recorder. Tc-99m gluceptate and Tc-99m sodium pertechnetate elute between 1 and 4 minutes under these conditions, whereas the Tc-99m labeled peptides eluted after a much greater amount of time. Peptides were detected by in-line spectrophotometric detection at 220nm.

Non-radioactive rhenium complexes were prepared by co-dissolving each of the peptide reagents of the invention with about one molar equivalent of tetrabutylammonium oxotetrabromorhenate (+5), prepared as described by Cotton et al. (1966, Inorg. Chem. 5: 9–16) in dimethylfonnamide or acetonitrile/water and stirred for 0.5–5 days. The rhenium complexes were isolated by reverse phase HPLC as described above for Tc-99m labeled peptides and were characterized by FABMS or ESMS. Non-radioactive peptides were detected as peptides by in-line spectrophotometric detection at 220 nm.

Radioactive rhenium complexes, using for example Re-186 or Re-188, are prepared from the appropriate perrhenate salts using the same protocol as for Tc-99m labeling, or by adding a reducing agent to a solution of the peptide and perrhenate, or optionally using a ligand transfer agent such as citrate and incubating the reaction at a temperature between room temperature and 100° C. for between 5 and 60 min.

Results of HPLC purification of peptides, Tc-99m labeled peptides and ReO-complexed peptides are shown in Table II.

Peptides of the invention, or ReO complexed embodiments thereof, were tested using in vitro assays that measure their ability to inhibit the specific binding of $^{125}$I-calcitonin to the calcitonin receptor, using membranes from rat brain and from T-47D cells (obtained from the American Type Culture Collection, Rockville, Md, ATCC Accession No. HTB-133), and on whole T47D or MCF-7 cells (ATCC Accession No. HTB-22). Such assays were used to identify high affinity peptide analogs of calcitonin. Breast cancer cell lines were screened for receptor expression and the best cell lines chosen for xenograft implantation in immune deficient mice. These tumor models were used to evaluate the tumor targeting potential in vivo of the high affinity peptides determined as the result of in vitro assays.

Assays using microsomal membrane fractions of rat brain and T47D cells were used to identify analogs with high affinity for the calcitonin receptor according to the method of Fisher et al. (1977, British J. Cancer 35: 777–784). Briefly, cells or tissue were washed in saline and homogenized. The membranes were washed several times, assayed for protein content and used in the binding assay. Membrane protein (or cells) were incubated with 0.1 μCi of $^{125}$I-calcitonin in the presence or absence of varying concentrations of the peptides of the invention or ReO complexes thereof. One hundred percent of the specific binding of $^{125}$I-calcitonin to the calcitonin receptor was determined to be the difference between total $^{125}$I-calcitonin binding and nonspecific binding of $^{125}$I-calcitonin measured in the presence of a receptor-saturating concentration of excess unlabeled salmon calcitonin (1 μM) The specific binding of 125I-calcitonin was measured in the presence of various concentrations of the peptides of the inventions and the rhenium complexes thereof to define the concentration at which these compounds inhibit specific binding of calcitonin by 50% (defined as the $IC_{50}$).

Using these assays, results for each of the tested compounds are shown in Table III. These results indicate that the peptides and ReO complexes of the peptide of the invention bind with high afinity to calcitonin receptor-expressing tumor cells and brain membranes.

TABLE II

| Peptide | Peptide | ReO Complex |
|---|---|---|
| CH₃CO.SNLST.Hhc.VLGKLSC(BAT)ELHKLQTYPRTNTGSGTP.amide | 13.7 | 15.6 |
| CH₃CO.SNLST.Hhc.VLGKLSQELHKLQTYPRTNTGSGTP(ε-K)GC.amide | 15.0 | 13.5 |
| CH₃CO.SNLST.Hhc.VLGKLSCELHKLQTYPRTNTGSGTP.amide | 19.2 | NA |
| CH₃CO.SNLST.Hhc.VLGKLSC(CH₂CO.GGCK.amide)ELHKLQTYPRTNTGSGTP.amide | 21.2 | 17.8 |
| CH₃CO.SNLST.Hhc.VLGKLSC(CH₂CO.(β-Dap)KCK.amide)ELHKLQTYPRTNTGSGTP.amide | 12.1 | 12.9 |
| CH₃CO.SNLST.Hhc.VLGKLSC(CH₂CO.(ε-K)GCE.amide)ELHKLQTYPRTNTGSGTP.amide | 11.9 | 12.4 |
| CH₃CO.SNLST.Hcy.VLGKLSCELHKLQTYPRTNTGSGTP.amide | 13.1 | NA |
| CH₃CO.SNLST.Hcy.VLGKLSC(CH₂CO.GGCK.amide)ELHKLQTYPRTNTGSGTP.amide | 12.4 | 13.5 |
| CH₃CO.SNLST.Hcy.VLGKLSC(CH₂CO.(β-Dap)KCK.amide)ELHKLQTYPRTNTGSGTP.amide | 11.0 | 11.8 |
| CH₃CO.SNLST.Hcy.VLGKLSC(CH₂CO.(ε-K)GCE.amide)ELHKLQTYPRTNTGSGTP.amide | 12.5 | 13.1 |
| CH₃CO.SNLST.Cys.VLGKLSCELHKLQTYPRTNTGSGTP.amide | 10.7 | NA |
| CH₃CO.SNLST.Cys.VLGKLSC(CH₂CO.GGCK.amide)ELHKLQTYPRTNTGSGTP.amide | 9.98 | 11.1 |
| CH₃CO.SNLST.Cys.VLGKLSC(CH₂CO.(β-Dap)KCK.amide)ELHKLQTYPRTNTGSGTP.amide | 8.23 | 9.2 |
| CH₃CO.SNLST.Cys.VLGKLSC(CH₂CO.(ε-K)GCE.amide)ELHKLQTYPRTNTGSGTP.amide | 9.98 | 10.7 |
| SNLST.Asu.VLGKLSCELHKLQTYPRTNTGSGTP.amide | 12.7 | NA |
| SNLST.Asu.VLGKLSC(CH₂CO.(β-Dap)KCK.amide)ELHKLQTYPRTNTGSGTP.amide | 10.7 | 11.4 |
| SNLST.Asu.VLGKLSCELHKLQTYPRTDVGAGTP.amide | 13.2 | NA |
| SNLST.Asu.VLGKLSC(CH₂CO.(β-Dap)KCK.amide)ELHKLQTYPRTDVGAGTP.amide | 11.1 | 11.7 |

Data represents HPLC retention times in minutes.

EXAMPLE 4
Biological Assays

Peptides of the invention, or ReO-complexed embodiments thereof, were assayed for biological activity in competition binding assays with $^{125}$I-labeled calcitonin.

Similar experiments are performed with other peptides of the invention using whole T47D and MCF-7 beast cancer cells. The cell binding assays are done essentially by the method of Findlay et al. (1990, J. Endocrinol. 130: 321–326.) Briefly, cells were washed in saline and resuspended in Hank's balanced salt solution. One to two million cells were incubated with 0.1 μCi $^{125}$I-calcitonin in the absence and presence of 1 μM unlabeled salmon calcitonin. Cells are incubated with 0.1 μCi of $^{125}$I-calcitonin in the presence or absence of varying concentrations of the peptides of the invention or ReO complexes thereof.

These data show that 86% (6 of 7) of the breast cancer cell lines assayed were positive for calcitonin receptors. Thus, the target receptor for the inventions are present in most breast cancer cell lines tested. These results indicate that the calcitonin peptides of the invention are appropriate for

TABLE III

Displacement of $^{125}$I-Calcitonin from CTR in T-47D and Rat Brain Membranes by CT-Mimetic Peptides

| Peptide Mimetic Structure | T-47D | | Rat brain | |
|---|---|---|---|---|
| | $IC_{50}$ | $K_i$ | $IC_{50}$ | $K_i$ |
| (CH$_2$CO.SNLST.Hhc).VLGKLSC(BAT)ELHKLQTYPRTNTGSGTP.amide | 0.53 | 0.41 | 2.6 | ND |
| (CH$_2$CO.SNLST.Hhc).VLGKLSQELHKLQTYPRTNTGSGTP(ε-K)GC.amide | 16 | 12 | 18 | ND |
| (CH$_2$CO.SNLST.Hhc).VLGKLSC(BAT)ELHKLQTYPRTNTGSGTP.amide(ReO) | 1.5 | 1.2 | 3.0 | ND |
| (CH$_2$CO.SNLST.Hhc).VLGKLSQELHKLQTYPRTNTGSGTP(ε-K)GC.amide(ReO) | 28 | 22 | 22 | ND |

TABLE IV

Displacement of 125 I-Calcitonin from T47D (Cells and Membranes) and MCF-7 Cells

| Sequence | $IC_{50}$ (nM)$^x$ | $IC_{50}$ (nM)$^y$ | $IC_{50}$ (nM)$^z$ |
|---|---|---|---|
| CH$_2$CO.SNLST.Hhc.VLKGKLSCELHKLQTYPRTNTGSGTP.amide | 1.6 | nd | nd |
| CH$_2$CO.SNLST.Hhc.VLGKLSC(CH$_2$CO.GGCK.amide)ELHKLQTYPRTNTGSGTP.amide | 2.6 | nd | nd |
| CH$_2$CO.SNLST.Hhc.VLGKLSC(CH$_2$CO.(β-Dap)KCK.amide)ELHKLQTYPRTNTGSGTP.amide.ReO | nd | 0.42 | 5.8 |
| CH$_2$CO.SNLST.Hhc.VLGKLSC(CH$_2$CO.(ε-K)GCE.amide)ELHKLQTYPRTNTGSGTP.amide.ReO | nd | 0.33 | 3.3 |
| CH$_2$CO.SNLST.Hcy.VLGKLSC(CH$_2$CO.GGCK.amide)ELHKLQTYPRTNTGSGTP.amide.ReO | nd | 0.83 | 4.8 |
| CH$_2$CO.SNLST.Hcy.VLGKLSC(CH$_2$CO.(β-Dap)KCK.amide)ALHKLQTYPRTNTGSGTP.amide.ReO | nd | 0.84 | nd |
| CH$_2$CO.SNLST.Hcy.VLGKLSC(CH$_2$CO.(ε-K)GCE.amide)ELHKLQTYPRTNTGSGTP.amide-ReO | nd | 0.89 | nd |
| CH$_2$CO.SNLST.Cys.VLGKLSC(CH$_2$CO.GGCK.amide)ELHKLQTYPRTNTGSGTP.amide.ReO | nd | 1.0 | 5.2 |
| CH$_2$CO.SNLST.Cys.VLGKLSC(CH$_2$CO.(β-Dap)KCK.amide)ELHKLQTYPRTNTGSGTP.amide.ReO | nd | 2.9 | nd |
| CH$_2$CO.SNLST.Cys.VLGKLSC(CH$_2$CO.(ε-K)GCE.amide)ELHKLQTYPRTNTGSGTP.amide.ReO | nd | 2.6 | 1.9 |
| SNLST.Asu.VLGKLSC(CH$_2$CO.(β-Dap)KCK.amide)ELHKLQTYPRTNTGSGTP.amide.ReO | nd | 2.7 | 8.0 |
| SNLST.Asu.VLGKLSC(CH$_2$CO.(β-Dap)KCK.amide)ELHKLQTYPRTDVGAGTP.amide.ReO | nd | 0.55 | 7.0 |
| CSNLSTCVLGKLSQELHKLQTYPRTNTGSGTP-NH$_2$ (salmon calcitonin) | nd | nd | 12.3 | nd = not done
wherein:
x T47D cell membranes
y Whole T47D cells.
z Whole MCF-7 cells are determined as described above. Using these assays, results for each of the tested compounds are shown in Table IV.

These results indicated that the peptides and ReO complexes of the peptides of the invention were potent inhibitors of calcitonin binding in two different calcitonin receptor-expressing breast tumor cell lines. These results further demonstrate that the calcitonin peptides and ReO complexes provided by the invention were capable of specifically binding to calcitonin receptors.

The binding of $^{125}$I-calcitonin to whole cells was used to assess the calcitonin receptor density in seven different breast cancer cell lines. The site density per cell was determined for MCF-7 cells in the presence of different concentrations of calcitonin to acheive saturation of the receptors. The data was then linearized by the method of Scatchard et al. (1949, N.Y. Acad. Sci. 51: 600–672) to determine $K_d$ and $B_{max}$, values (to estimate receptor density). Other cells were compared to MCF-7 cells at a single concentration of $^{125}$I-calcitonin and their calcitonin receptor density estimated thereby. The data are summarized in FIG. 1.

preparing useful scintigraphic imaging agents for the imaging of tumor sites in humans.

Calcitonin receptor expressing breast cancer cells (T47D and MCF-7) are implanted into immune deficient mice and allowed to grow tumors. For testing new $^{99m}$Tc-calcitonin peptides, tumor-bearing mice are injected with approximately 1 mCi at approximately 20 mCi/10 nmol Tc-99m labeled peptide. The mice are cervically dislocated and imaged statically for 5 minutes using a gamma camera. The biodistribution of the $^{99m}$Tc-calcitonin peptides are then determined by counting blood, tumor, target organs and muscle in a gamma counter along with standard aliquots of the injected dose. To assess the tumor imaging potential of selected analogs the ratio of radioactivity in blood and muscle are compared to that in tumor. The time points for biodistribution are chosen to represent early, middle and late phases of $^{99m}$Tc-calcitonin analog clearance.

It should be understood that the foregoing disclosure emphasizes certain specific embodiments of the invention and that all modifications or alternatives equivalent thereto are within the spirit and scope of the invention as set forth in the appended claims.

We claim:

1. A synthetic, calcitonin receptor-binding peptide having a molecular weight of less than about 10,000 daltons, a carboxyl terminus of said peptide being covalently linked to a radiometal chelator to form a reagent wherein:

said reagent has a binding affinity for a calcitonin receptor of not less than about one-tenth the binding affinity of radioiodinated native calcitonin for said receptor.

2. The reagent of claim 1, wherein the chelator is selected from the group consisting of:

a) a chelator comprising a single thiol-containing moiety of formula:

$$A\text{-CZ(B)-}\{C(R^1R^2)\}_n\text{-X}$$

wherein A is H, HOOC, $H_2$NOC, (amino acid or peptide)-NHOC, (amino acid or peptide)-OOC or $R^4$;

B is H, SH, —$NHR^3$, —$N(R^3)$-(amino acid or peptide), or $R^4$;

X is H, SH, —$NHR^3$, —$N(R^3)$-(amino acid or peptide) or $R^4$;

Z is H or $R^4$;

$R^1$, $R^2$, $R^3$ and $R^4$ are independently H or lower straight or branched chain or cyclic alkyl;

n is 0, 1 or 2;

(amino acid) is any primary α- or β-amino acid not containing a thiol group; and where B is —NHR³ or —N(R³)-(amino acid or peptide), X is SH, and n is 1 or 2;
where X is —NHR³ or —N(R³)-(amino acid or peptide), B is SH, and n is 1 or 2;
where B is H or R⁴, A is HOOC, H₂NOC, (amino acid or peptide)-NHOC, or (amino acid or peptide)-OOC; X is SH; and n is 0 or 1;
where A is H or R⁴, then where B is SH, X is —NHR³ or —N(R³)-(amino acid or peptide) and where X is SH, B is —NHR³ or —N(R³)-(amino acid or peptide) and n is 1 or 2;
where X is H or R⁴, A is HOOC, H₂NOC, (amino acid or peptide)-NHOC, or (amino acid or peptide)-OOC; and B is SH;
where Z is methyl, X is methyl; A is HOOC, H₂NOC, (amino acid or peptide)-NHOC, or (amino acid or peptide)-OOC; B is SH and n is 0;
where B is SH, X is not SH and where X is SH, B is not SH;
and wherein the thiol moiety is in the reduced form;

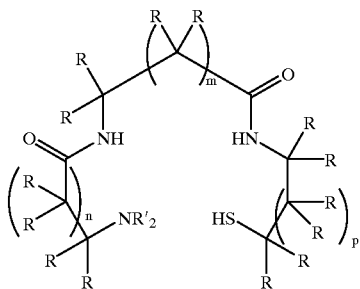

wherein: n, m and p are each independently 0 or 1,
each R' is independently H, lower alkyl, hydroxyalkyl (C₂–C₄), or alkoxyalkyl (C₂–C₄);
each R is independently H or R", where R" is substituted or unsubstituted lower alkyl or phenyl not comprising a thiol group;
one R or R' is L, wherein when an R' is L, —NR'₂ is an amine; and L is a bivalent group linking the chelator to the peptide; and

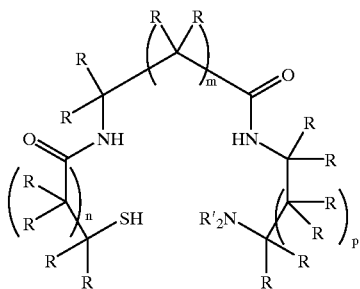

wherein: n, m and p are each independently 0 or 1,
each R' is independently H, lower alkyl, hydroxyalkyl (C₂–C₄), or alkoxyalkyl (C₂–C₄);
each R is independently H or R", where R" is substituted or unsubstituted lower alkyl or phenyl not comprising a thiol group;
one R or R' is L, wherein when an R' is L, —NR'₂ is an amine; and L is a bivalent group linking the chelator to the peptide.

3. The reagent of claim 2, wherein the chelator is selected from the group consisting of:

—(amino acid)¹-(amino acid)²-{A-CZ(B)-{C(R¹R²)}ₙ-X};
—{A-CZ(B)-{C(R¹R²)}ₙ-X}-(amino acid)¹-(amino acid)²;
—(a primary α,β- or β,γ-diamino acid)-(amino acid)¹-{A-CZ(B)-{C(R¹R²)}ₙ-X}; and
—{A-CZ(B)-{C(R¹R²)}ₙ-X}-(amino acid)¹-(a primary α,β- or α,γ-diamino acid);
wherein (amino acid)¹ and (amino acid)² are each independently any naturally-ocurring, modified, substituted or altered α- or β-amino acid not containing a thiol group.

4. The reagent of claim 3, wherein the chelator is selected from the group consisting of:
(amino acid)¹-(amino acid)²-cysteine;
(amino acid)¹-(amino acid)²-isocysteine-;
(amino acid)¹-(amino acid)²-homocysteine-;
(amino acid)¹-(amino acid)²-penicillamine-;
(amino acid)¹-(amino acid)²-2-mercaptoethylamine-;
(amino acid)¹-(amino acid)²-2-mercaptopropylamine-;
(amino acid)¹-(amino acid)²-2-mercapto-2-methylpropylamine-; and
(amino acid)¹-(amino acid)²-3-mercaptopropylamine-;
wherein a side chain of said chelator is covalently bonded to the peptide.

5. The reagent of claim 4, wherein (amino acid)¹ is selected from the group consisting of an α,β-diamino acid having a free α-amine and a β,γ-diamino acid having a free β- amine.

6. The reagent of claim 3, wherein the chelator is selected from the group consisting of:
—cysteine-(amino acid)-(α,β- or β,γ-diamino acid);
—isocysteine-(amino acid)-(α,β- or β,γ-diamino acid);
—homocysteine-(amino acid)-(α,β- or β,γ-diamino acid);
—penicillamine-(amino acid)-(α,β- or β,γ-diamino acid);
2-mercaptoacetic acid-(amino acid)-(α,β- or β,γ-diamino acid);
2- or 3-mercaptopropionic acid-(amino acid)-(α,β- or β,γ-diamino acid); and
2-mercapto-2-methylpropionic acid-(amino acid)-(α,β- or β,γ-diamino acid);
wherein an amino terminus or a side chain of said chelator is covalently bonded to the peptide.

7. The reagent of claim 1, wherein the chelator is selected from the group consisting of:
—Gly-Gly-Cys-;
—Ala-Gly-Cys-;
—(ε-Lys)-Gly-Cys-;
—(δ-Orn)-Gly-Cys-;
—(γ-Dab)-Gly-Cys-;
—(β-Dap)-Lys-Cys-;
—(β-Dap)-Gly-Cys-; and
—Cys(BAT).

8. The reagent of claim 2, having a formula:

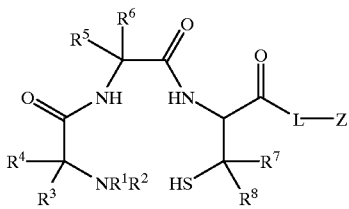

wherein:
R¹ and R² are each independently H, lower alkyl, hydroxyalkyl ($C_2$–$C_4$) or alkoxyalkyl ($C_2$–$C_4$);
R³, R⁴, R⁵, and R⁶ are independently H, substituted or unsubstituted lower alkyl or phenyl not comprising a thiol group;
R⁷ and R⁸ are each independently H, lower alkyl, lower hydroxyalkyl or lower alkoxyalkyl;
L is a bivalent linking moiety; and
Z is the peptide.

9. The reagent of claim 2, having a formula:

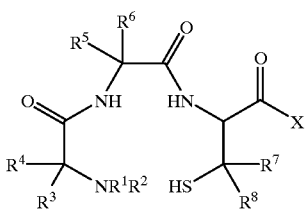

wherein:
R¹ and R² are each independently H, lower alkyl, hydroxyalkyl ($C_2$–$C_4$), or alkoxyalkyl ($C_2$–$C_4$);
R³, R⁴, R⁵, and R⁶ are independently H, substituted or unsubstituted lower alkyl or phenyl not comprising a thiol group, and one of R³, R⁴, R⁵, and R⁶ is Z—L—($CR_2$)$_n$—;
R⁷ and R⁸ are each independently H, lower alkyl, lower hydroxyalkyl or lower alkoxyalkyl;
L is a bivalent linking moiety;
Z is the peptide; and
X is —$NH_2$, —$NR^1R^2$, or —$NR^1$—Y, where Y is an amino acid, an amino acid amide, or a peptide having from 2 to about 20 amino acids.

10. The reagent of claim 2, having a formula:

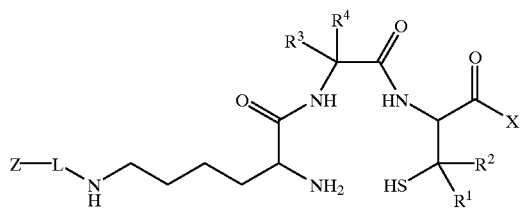

wherein: R¹ and R² are each independently H, lower alkyl, hydroxyalkyl ($C_2$–$C_4$) or alkoxyalkyl ($C_2$–$C_4$);
R³, R⁴, R⁵, and R⁶ are independently H, substituted or unsubstituted lower alkyl or phenyl not comprising a thiol group;
n is an integer from 1 to 6;
L is a bivalent linking moiety; and
Z is the peptide.

11. The reagent of claim 2, having a formula:

wherein:
L is a linker group; and
Z is the peptide.

12. A scintigraphic imaging agent comprising the reagent of any of claims 1 through 11 and technetium-99m.

13. A composition comprising the reagent of any of claims 1 through 11 and a stannous ion.

14. A radiotherapeutic agent comprising the reagent of any of claims 1 through 11 and a cytotoxic radioisotope.

15. The agent of claim 14, wherein the radioisotope is selected from the group consisting of rhenium-186 and rhenium-188.

16. A complex formed by reacting the reagent of any of claims 1 through 11 with technetium-99m, rhenium-186 or rhenium-188 in the presence of a reducing agent.

17. A complex formed by labeling the reagent of any of claims 1 through 11 with technetium-99m by ligand exchange of a prereduced technetium-99m complex.

18. A complex formed by labeling the reagent of any of claims 1 through 11 with rhenium-186 or rhenium-188 by ligand exchange of a prereduced rhenium complex.

19. A kit for preparing a radiopharmaceutical preparation, said kit comprising a sealed vial containing a predetermined quantity of the reagent of any of claims 1 through 11 and a sufficient amount of a reducing agent to label the reagent with technetium-99m, rhenium-186 or rhenium-188.

20. A synthetic, calcitonin receptor-binding peptide having a molecular weight of less than about 10,000 daltons, a carboxyl terminus of said peptide being covalently linked to a radiometal chelator to form a reagent wherein:
said reagent has a binding affinity for a calcitonin receptor equal to or greater than the binding affinity of radioiodinated native calcitonin for said receptor.

21. The reagent of claim 20, wherein the chelator is selected from the group consisting of:
a) a chelator comprising a single thiol-containing moiety of formula:

$$A\text{-}CZ(B)\text{-}\{C(R^1R^2)\}_n\text{-}X$$

wherein A is H, HOOC, $H_2$NOC, (amino acid or peptide)-NHOC, (amino acid or peptide)-OOC or R⁴;
B is H, SH, —NHR³, —N(R³)-(amino acid or peptide), or R⁴;
X is H, SH, —NHR³, —N(R³)-(amino acid or peptide) or R⁴;
Z is H or R⁴;
R¹, R², R³ and R⁴ are independently H or lower straight or branched chain or cyclic alkyl;
n is 0, 1 or 2;
(amino acid) is any primary α- or β-amino acid not containing a thiol group; and
where B is —NHR³ or —N(R³)-(amino acid or peptide), X is SH, and n is 1 or 2;

where X is —NHR$^3$ or —N(R$^3$)-(amino acid or peptide), B is SH, and n is 1 or 2;
where B is H or R$^4$, A is HOOC, H$_2$NOC, (amino acid or peptide)-NHOC, or (amino acid or peptide)-OOC; X is SH; and n is 0 or 1;
where A is H or R$^4$, then where B is SH, X is —NHR$^3$ or —N(R$^3$)-(amino acid or peptide) and where X is SH, B is —NHR$^3$ or —N(R$^3$)-(amino acid or peptide) and n is 1 or 2;
where X is H or R$^4$, A is HOOC, H$_2$NOC, (amino acid or peptide)-NHOC, or (amino acid or peptide)-OOC; and B is SH;
where Z is methyl, X is methyl; A is HOOC, H$_2$NOC, (amino acid or peptide)-NHOC, or (amino acid or peptide)-OOC; B is SH and n is 0;
where B is SH, X is not SH and where X is SH, B is not SH;
and wherein the thiol moiety is in the reduced form;

b)

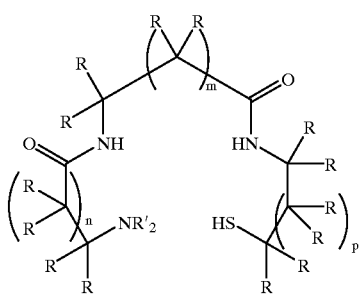

wherein: n, m and p are each independently 0 or 1,
each R' is independently H, lower alkyl, hydroxyalkyl (C$_2$–C$_4$), or alkoxyalkyl (C$_2$–C$_4$);
each R is independently H or R", where R" is substituted or unsubstituted lower alkyl or phenyl not comprising a thiol group;
one R or R' is L, wherein when an R' is L, —NR'$_2$ is an amine; and
L is a bivalent group linking the chelator to the peptide; and c)

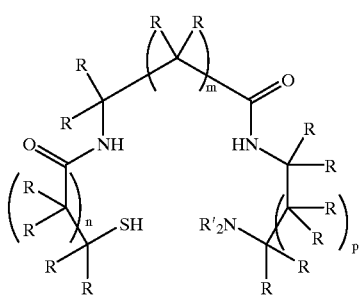

wherein: n, m and p are each independently 0 or 1,
each R' is independently H, lower alkyl, hydroxyalkyl (C$_2$–C$_4$), or alkoxyalkyl (C$_2$–C$_4$);
each R is independently H or R", where R" is substituted or unsubstituted lower alkyl or phenyl not comprising a thiol group;
one R or R' is L, wherein when an R' is L, —NR'$_2$ is an amine; and
L is a bivalent group linking the chelator to the peptide.

22. The reagent of claim 21, wherein the chelator is selected from the group consisting of:
—(amino acid)$^1$-(amino acid)$^2$-{A-CZ(B)-{C(R$^1$R$^2$)}$_n$-X};
—{A-CZ(B)-{C(R$^1$R$^2$)}$_n$-X}-(amino acid)$^1$-(amino acid)$^2$;
—(a primary α,β- or β,γ-diamino acid)-(amino acid)$^1$-{A-CZ(B)-{C(R$^1$R$^2$)}$_n$-X}; and
—{A-CZ(B)-{C(R$^1$R$^2$)}$_n$-X}-(amino acid)$^1$-(a primary α,β- or α,γ-diamino acid);
wherein (amino acid)$^1$ and (amino acid)$^2$ are each independently any naturally-ocurring, modified, substituted or altered α- or β-amino acid not containing a thiol group.

23. The reagent of claim 22, wherein the chelator is selected from the group consisting of:
(amino acid)$^1$-(amino acid)$^2$-cysteine;
(amino acid)$^1$-(amino acid)$^2$-isocysteine-;
(amino acid)$^1$-(amino acid)$^2$-homocysteine-;
(amino acid)$^1$-(amino acid)$^2$-penicillamine-;
(amino acid)$^1$-(amino acid)$^2$-2-mercaptoethylamine-;
(amino acid)$^1$-(amino acid)$^2$-2-mercaptopropylamine-;
(amino acid)$^1$-(amino acid)$^2$-2-mercapto-2-methylpropylamine-; and
(amino acid)$^1$-(amino acid)$^2$-3-mercaptopropylamine-;
wherein a side chain of said chelator is covalently bonded to the peptide.

24. The reagent of claim 23, wherein (amino acid)$^1$ is selected from the group consisting of an α,β-diamino acid having a free α-amine and a β,γ-diamino acid having a free β-amine.

25. The reagent of claim 21, wherein the chelator is selected from the group consisting of:
—cysteine-(amino acid)-(α,β- or β,γ-diamino acid);
—isocysteine-(amino acid)-(α,β- or β,γ-diamino acid);
—homocysteine-(amino acid)-(α,β- or β,γ-diamino acid);
—penicillamine-(amino acid)-(α,β,- or β,γ-diamino acid);
2-mercaptoacetic acid-(amino acid)-(α,β- or β,γ-diamino acid);
2- or 3-mercaptopropionic acid-(amino acid)-(α,β- or β,γ-diamino acid); and
2-mercapto-2-methylpropionic acid-(amino acid)-(α,β- or β,γ-diamino acid);
wherein an amino terminus or a side chain of said chelator is covalently bonded to the peptide.

26. The reagent of claim 20, wherein the chelator is selected from the group consisting of:
—Gly-Gly-Cys-;
—Ala-Gly-Cys-;
—(ε-Lys)-Gly-Cys-;
—(δ-Orn)-Gly-Cys-;
—(γ-Dab)-Gly-Cys-;
—(β-Dap)-Lys-Cys-;
—(β-Dap)-Gly-Cys-; and
—Cys(BAT).

27. The reagent of claim 21, having a formula:

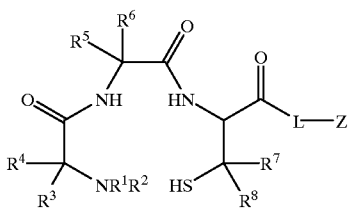

wherein:

$R^1$ and $R^2$ are each independently H, lower alkyl, hydroxyalkyl ($C_2$–$C_4$) or alkoxyalkyl ($C_2$–$C_4$);

$R^3$, $R^4$, $R^5$, and $R^6$ are independently H, substituted or unsubstituted lower alkyl or phenyl not comprising a thiol group;

$R^7$ and $R^8$ are each independently H, lower alkyl, lower hydroxyalkyl or lower alkoxyalkyl;

L is a bivalent linking moiety; and

Z is the peptide.

28. The reagent of claim 21, having a formula:

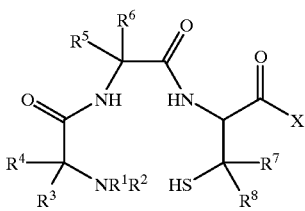

wherein:

$R^1$ and $R^2$ are each independently H, lower alkyl, hydroxyalkyl ($C_2$–$C_4$), or alkoxyalkyl ($C_2$–$C_4$);

$R^3$, $R^4$, $R^5$, and $R^6$ are independently H, substituted or unsubstituted lower alkyl or phenyl not comprising a thiol group, and one of $R^3$, $R^4$, $R^5$, and $R^6$ is Z—L—($CR_2$)$_n$—;

$R^7$ and $R^8$ are each independently H, lower alkyl, lower hydroxyalkyl or lower alkoxyalkyl;

L is a bivalent linking moiety;

Z is the peptide; and

X is —$NH_2$, —$NR^1R^2$, or —$NR^1$-Y, where Y is an amino acid, an amino acid amide, or a peptide having from 2 to about 20 amino acids.

29. The reagent of claim 21, having a formula:

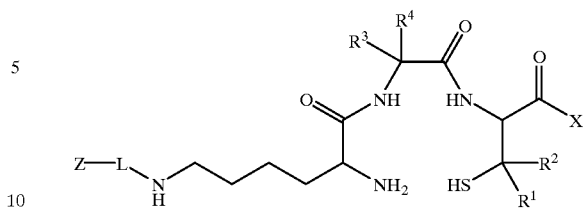

wherein: $R^1$ and $R^2$ are each independently H, lower alkyl, hydroxyalkyl ($C_2$–$C_4$) or alkoxyalkyl ($C_2$–$C_4$);

$R^3$, $R^4$, $R^5$, and $R^6$ are independently H, substituted or unsubstituted lower alkyl or phenyl not comprising a thiol group;

n is an integer from 1 to 6;

L is a bivalent linking moiety; and

Z is the peptide.

30. The reagent of claim 21, having a formula:

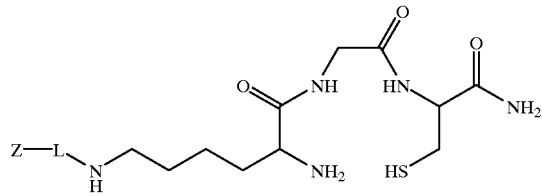

wherein:

L is a linker group; and

Z is the peptide.

31. A scintigraphic imaging agent comprising the reagent of any of claim 20 through 30 and technetium-99m.

32. A composition comprising the reagent of any of claims 20 through 30 and a stannous ion.

33. A radiotherapeutic agent comprising the reagent of any of claims 20 through 30 and a cytotoxic radioisotope.

34. The agent of claim 33, wherein the radioisotope is selected from the group consisting of rhenium-186 and rhenium-188.

35. A complex formed by reacting the reagent of any of claims 20 through 30 with technetium-99m, rhenium-186 or rhenium-188 in the presence of a reducing agent.

36. A complex formed by labeling the reagent of any of claims 20 through 30 with technetium-99m by ligand exchange of a prereduced technetium-99m complex.

37. A complex formed by labeling the reagent of any of claims 20 through 30 with rhenium-186 or rhenium-188 by ligand exchange of a prereduced rhenium complex.

38. A kit for preparing a radiopharmaceutical preparation, said kit comprising a sealed vial containing a predetermined quantity of the reagent of any of claims 20 through 30 and a sufficient amount of a reducing agent to label the reagent with technetium-99m, rhenium-186 or rhenium-188.

* * * * *